(12) United States Patent
Huang et al.

(10) Patent No.: US 11,021,464 B2
(45) Date of Patent: Jun. 1, 2021

(54) CRYSTALLINE FORMS OF 4-(TERT-BUTOXYAMINO)-6-(6-(TRIFLUOROMETHYL)PYRIDIN-2-YL)-N-(2-(TRIFLUOROMETHYL)PYRIDIN-4-YL)-1,3,5-TRIAZIN-2-AMINE METHANESULFONIC ACID SALT

(71) Applicants: CHIA TAI TIANQING PHARMACEUTICAL GROUP CO., LTD., Lianyungang (CN); LIANYUNGANG RUNZHONG PHARMACEUTICAL CO., LTD., Lianyungang (CN); CENTAURUS BIOPHARMA CO., LTD., Beijing (CN)

(72) Inventors: Ticong Huang, Lianyungang (CN); Huifeng Xiao, Lianyungang (CN); Rui Zhao, Lianyungang (CN); Fei Liu, Lianyungang (CN); Wei Wei, Lianyungang (CN); Hongjiang Xu, Lianyungang (CN); Xiaojin Wang, Lianyungang (CN); Jingli Wu, Lianyungang (CN)

(73) Assignees: Chia Tai Tianqing Pharmaceutical Group Co., Ltd., Lianyungang (CN); Lianyungang Runzhong Pharmaceutical Co., Ltd, Lianyungang (CN); Centaurus Biopharma Co., Ltd, Beijing (CN)

( * ) Notice: Subject to any disclaimer, the term of this patent is extended or adjusted under 35 U.S.C. 154(b) by 0 days.

(21) Appl. No.: 16/479,459

(22) PCT Filed: Jan. 22, 2018

(86) PCT No.: PCT/CN2018/073578
§ 371 (c)(1),
(2) Date: Jul. 19, 2019

(87) PCT Pub. No.: WO2018/133856
PCT Pub. Date: Jul. 26, 2018

(65) Prior Publication Data
US 2019/0352281 A1 Nov. 21, 2019

(30) Foreign Application Priority Data
Jan. 22, 2017 (CN) .......................... 201710047243.4
Jul. 13, 2017 (CN) .......................... 201710570764.8

(51) Int. Cl.
*A61K 31/53* (2006.01)
*C07D 251/18* (2006.01)
*C07D 401/14* (2006.01)

(52) U.S. Cl.
CPC ........ *C07D 401/14* (2013.01); *C07B 2200/13* (2013.01)

(58) Field of Classification Search
CPC ..... C07D 401/14; C07D 251/18; A61K 31/53
USPC .......................................... 514/245; 544/209
See application file for complete search history.

(56) References Cited

U.S. PATENT DOCUMENTS

2019/0062308 A1* 2/2019 Zhao ....................... A61K 31/53
2019/0161473 A1* 5/2019 Wang ..................... C07D 417/14

FOREIGN PATENT DOCUMENTS

| CA | 2993687 A1 * | 2/2017 | .......... C07D 401/14 |
| CA | 2993687 A1 | 2/2017 | |
| CN | 104114543 A | 10/2014 | |
| CN | 107641114 A | 1/2018 | |
| EP | 3489230 A1 | 5/2019 | |
| WO | 2013102431 A1 | 7/2013 | |
| WO | 2017016513 A1 | 2/2017 | |
| WO | WO-2017016513 A1 * | 2/2017 | .......... C07D 251/26 |
| WO | PCT/CN2016/092254 | * | 7/2017 | |
| WO | PCT/CN2017/093597 | * | 7/2017 | |
| WO | WO-2018014852 A1 * | 1/2018 | .......... A61K 31/444 |

OTHER PUBLICATIONS

S. Datta et al., 3 Nature Reviews | Drug Discovery, 42-57 (2004) (Year: 2004).*
L.D. Bighley et al., Salt Forms and Absorption, in 13 Encyclopedia of Pharmaceutical Technology 453 (M Swarbrick and J. Boylan eds., 1996) (Year: 1996).*
S.L. Morissette et al., 56 Advanced Drug Delivery Reviews, 275-300, 276 (2004) (Year: 2004).*
Solid State Characterization of Pharmaceuticals 473-491, 490 (R.A. Storey et al., eds., 2011) (Year: 2011).*

(Continued)

*Primary Examiner* — Douglas M Willis
(74) *Attorney, Agent, or Firm* — Kilpatrick Townsend & Stockton LLP

(57) ABSTRACT

The invention discloses a crystal of 4-(tert-butoxyamino)-6-(6-(trifluoromethyl)pyridin-2-yl)-N-(2-(trifluoromethyl)pyridin-4-yl)-1,3,5-triazin-2-amine compound, a mesylate salt and crystal thereof, a preparation method thereof, a composition containing thereof, and a use thereof for inhibiting activity of mutant IDH2 and treating cancer.

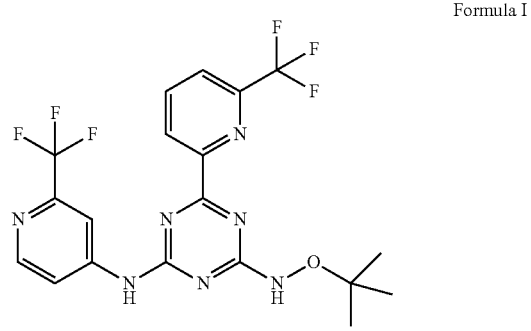

Formula I

20 Claims, 10 Drawing Sheets

(56) References Cited

OTHER PUBLICATIONS

S. Badaway et al., Salt Selection for Pharmaceutical Compounds, in Preformulation in Solid Dosage Form Dev. 63 (M. Adeyeye ed., 2008) (Year: 2008).*
R.J. Bastin et al., Salt Selection and Optimization Procedures for Pharmaceutical New Chemical Entities, 4 Organic Process Res. Dev. 427 (2000) (Year: 2000).*
P.L. Gould, Salt Selection for Basic Drugs, 33 Int. J. Therapeutics 201, 217 (1986) (Year: 1986).*
K. R. Morris et al., An Integrated Approach to the Selection of Optimal Salt Form for a New Drug Candidate, 105 Int'l. J. Pharm. 209 (1994) (Year: 1994).*
K. Chow et al., Engineering of Pharmaceutical Materials: an Industrial Perspective, 97 J. Pharmaceutical Sciences, 2855 (2008) (Year: 2008).*
English-language translation of US PCT/CN2016/092254 (2016) (Year: 2016).*
A.J. Cruz-Cabeza et al., 44 Chemical Society Reviews, 8619-8635 (2015) (Year: 2015).*
English-language translation of PCT/CN2017/093597 (2017) (Year: 2017).*
International Search Report in PCT/CN2018/073578, dated Apr. 26, 2018.
Inoue, et al. "Syntheses of Phenylazo-1, 3, 5-Triazines by the Oxidative Coupling of Hydrazino-1, 3, 5-Triazines With N, N-Disubstituted Anilines." Chemistry Letters 10, No. 12 (1981): 1733-1736.
Tedford, et al. "In silico screening for compounds that match the pharmacophore of omega-hexatoxin-Hv1 a leads to discovery and optimization of a novel class of insecticides." Pesticide biochemistry and physiology 106, No. 3 (2013): 124-140.

* cited by examiner

CRYSTALLINE FORMS OF 4-(TERT-BUTOXYAMINO)-6-(6-(TRIFLUOROMETHYL)-PYRIDIN-2-YL)-N-(2-(TRIFLUOROMETHYL)-PYRIDIN-4-YL)-1,3,5-TRIAZIN-2-AMINE METHANESULFONIC ACID SALT

CROSS REFERENCE TO RELATED APPLICATIONS

The present application is a U.S. National Stage Application of PCT/CN2018/073578, International Filing Date Jan. 1, 2018; which claims the priorities to and benefits of the priority to Chinese patent applications No. 201710047243.4, filed Jan. 22, 2017 and No. 201710570764.8 filed Jul. 13, 2017 with the China National Intellectual Property Administration on Jan. 22, 2017 and Jul. 13, 2017, respectively, which are incorporated herein by reference in their entireties.

TECHNICAL FIELD

The present invention belongs to the field of medical chemistry, and relates to a salt of a 1,3,5-triazine derivative and a crystal thereof, and more particularly, to a salt of 4-(tert-butoxyamino)-6-(6-(trifluoromethyl)pyridin-2-yl)-N-(2-(trifluoromethyl)pyridin-4-yl)-1,3,5-triazin-2-amine and a crystal thereof. The present invention also relates to processes for preparing the salt of the 1,3,5-triazine derivative and the crystal thereof, a pharmaceutical composition and use thereof.

BACKGROUND

As the most important key enzyme in intracellular tricarboxylic acid cycle, IDH (full name: isocitrate dehydrogenase) can catalyze the oxidative decarboxylation of isocitric acid to 2-oxoglutarate (i.e., α-ketoglutaric acid). Researches have shown that many tumors (such as, glioma, sarcoma, and acute myelocytic leukemia) have an IDH mutation at arginine residue in a catalytic center (IDH1/R132H, IDH2/R140Q, and IDH2/R172K). IDH2 mutations occur in approximately 15% of the patients with acute myeloid leukemia (AML), and mutation rate increases with age.

Enasidenib (AG-221), the first IDH2 inhibitor co-developed by Agios and Celgene, has an overall response rate (ORR) up to 41% and a complete remission rate (CR) up to 27% after the treatment to relapsed and refractory AML. 76% of the effective patients insist on the treatment for at least 6 months, and 44% of them have a stable condition.

The chemical stability, solid-state stability, in vivo metabolic properties and shelf life of an active ingredient are very important factors for an identified active compound for commercial use. Therefore, it is very important for the production and storage of a drug to provide a suitable form of the drug having desired properties.

SUMMARY OF THE INVENTION

The present invention provides a 1,3,5-triazine derivative represented by Formula I, which has a chemical name of 4-(tert-butoxyamino)-6-(6-(trifluoromethyl)pyridin-2-yl)-N-(2-(trifluoromethyl) pyridin-4-yl)-1,3,5-triazin-2-amine,

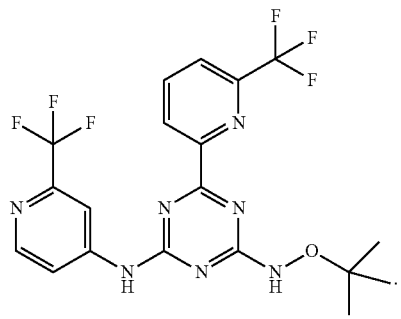

Formula I

The objects of the present invention are to provide a crystal of the compound of Formula I, a salt of the compound of Formula I and a crystal thereof. The crystal of the compound of Formula I, the salt of the compound of Formula I and the crystal thereof have high stability, low hygroscopicity, good in vivo metabolic level, and long half-life, and they have a good inhibiting activity against IDH2, have good properties in terms of physical properties, safety and metabolic stability, and have a high value as a drug.

The present invention relates to a crystal of the compound of Formula I.

In an aspect, the present invention provides a crystalline Form A of the compound of Formula I, characterized in that an X-ray powder diffraction spectrum thereof has diffraction peaks expressed by 2θ values at about 10.1°, 16.1°, 17.5°, 18.9° and 21.7°; typically has diffraction peaks expressed by 2θ values at about 10.1°, 16.1°, 17.5°, 18.9°, 21.7°, 23.5°, 24.4° and 26.2°; more typically has diffraction peaks expressed by 2θ values at about 10.1°, 16.1°, 17.5°, 18.9°, 21.7°, 22.4°, 22.8°, 23.5°, 24.0°, 24.4°, 26.2° and 29.8°; and even more typically has diffraction peaks expressed by 2θ values at about 10.1°, 12.3°, 14.3°, 14.6°, 16.1°, 17.5°, 18.9°, 19.7°, 20.1°, 21.7°, 22.4°, 22.8°, 23.5°, 24.0°, 24.4°, 26.2° and 29.8°.

As an embodiment of the present invention, the peak positions and intensities of the characteristic peaks in the X-ray powder diffraction spectrum of the crystalline Form A of the compound of Formula I according to the present invention have the characteristics shown in Table 1:

TABLE 1

| No. | 2θ(°) | Relative Intensity(I/I$_0$) |
|---|---|---|
| 1 | 10.1 | 78.9 |
| 2 | 12.3 | 10.2 |
| 3 | 14.3 | 8.9 |
| 4 | 14.6 | 7.7 |
| 5 | 16.1 | 42.4 |
| 6 | 17.5 | 51.6 |
| 7 | 18.9 | 100 |
| 8 | 19.7 | 10.5 |
| 9 | 20.1 | 11.8 |
| 10 | 21.7 | 74.2 |
| 11 | 22.4 | 14.5 |
| 12 | 22.8 | 16.5 |
| 13 | 23.5 | 26.8 |
| 14 | 24.0 | 15.6 |
| 15 | 24.4 | 28.1 |
| 16 | 26.2 | 37.8 |
| 17 | 29.8 | 13.3 |

In some embodiments of the present invention, the crystalline Form A of the compound of Formula I has an X-ray powder diffraction pattern substantially as shown in FIG. 1.

Without limitation, the present invention provides a typical example of a differential scanning calorimetry (DSC) measurement pattern of the crystalline Form A of the compound of Formula I, the heat flow from the sample is plotted as a function of temperature in the DSC pattern, and the rate of temperature change is about 10° C./min. The DSC pattern is characterized in that it has an absorption peak at about 224.8° C.

In another aspect, the present invention provides a process for preparing the crystalline Form A of the compound of Formula I, comprising: dissolving the compound of Formula I in an organic solvent at room temperature to obtain a clear solution, concentrating the solution under reduced pressure and drying to obtain the crystalline Form A of the compound of Formula I. In the process, the organic solvent is selected from the group consisting of methanol, ethanol, isopropanol, tert-butanol, acetone, tetrahydrofuran, acetonitrile and 1,4-dioxane, and mixed solvents of more than one solvent selected from the above-mentioned solvents in any ratio. In some embodiments, the organic solvent is selected from the group consisting of tetrahydrofuran, 1,4-dioxane, and a mixed solvent thereof.

In some embodiments of the above preparation process, the molar volume ratio of the compound of Formula I to the organic solvent is 1 mmol: 5 to 15 mL, or 1 mmol: 5 to 10 mL.

In yet another aspect, the present invention provides another process for preparing the crystalline Form A of the compound of Formula I, comprising: slurring the compound of Formula I in an organic solvent, filtering and drying to obtain the crystalline Form A of the compound of Formula I. In the process, the organic solvent is selected from the group consisting of dichloromethane, ethyl ether, methyl tert-butyl ether, ethylene glycol dimethyl ether, n-hexane, n-heptane and n-octane, and mixed solvents of more than one solvent selected from the above-mentioned solvents in any ratio. In some embodiments, the organic solvent is selected from the group consisting of dichloromethane, methyl tert-butyl ether, n-heptane, and mixed solvents of more than one solvent selected from the above-mentioned solvents.

In some embodiments of the above another preparation process, the molar volume ratio of the compound of Formula I to the organic solvent is 1 mmol: 2 to 10 mL, or 1 mmol: 2 to 5 mL.

In some embodiments of the above another preparation process, the slurring may be conducted at 0 to 50° C. or at the reflux temperature of the organic solvent during the above preparation of the crystalline Form A of the compound of Formula I; in some embodiments, the slurring is conducted at 25 to 30° C. or at the reflux temperature of the organic solvent.

In a further aspect, the present invention provides a crystalline Form B of the compound of Formula I, characterized in that an X-ray powder diffraction spectrum thereof has diffraction peaks expressed by 2θ values at about 10.0°, 17.4°, 18.8°, 24.3° and 26.1°; typically has diffraction peaks expressed by 2θ values at about 10.0°, 17.4°, 18.8°, 21.6°, 24.3° and 26.1°; more typically has diffraction peaks expressed by 2θ values at about 10.0°, 15.7°, 17.4°, 18.8°, 19.8°, 21.6°, 23.4°, 24.3° and 26.1°; and even more typically has diffraction peaks expressed by 2θ values at about 10.0°, 12.2°, 14.5°, 15.7°, 17.4°, 18.8°, 19.8°, 21.6°, 23.4°, 24.3°, 26.1° and 29.7°.

As an embodiment of the present invention, the peak positions and intensities of the characteristic peaks in the X-ray powder diffraction spectrum of the crystalline Form B of the compound of Formula I according to the present invention have the characteristics shown in Table 2:

TABLE 2

| No. | 2θ(°) | Relative Intensity($I/I_0$) |
|---|---|---|
| 1 | 10.0 | 100 |
| 2 | 12.2 | 7.7 |
| 3 | 14.5 | 5.9 |
| 4 | 15.7 | 11.9 |
| 5 | 17.4 | 39.6 |
| 6 | 18.8 | 39.5 |
| 7 | 19.8 | 10.5 |
| 8 | 21.6 | 27.9 |
| 9 | 23.4 | 16.7 |
| 10 | 24.3 | 32.8 |
| 11 | 26.1 | 31.2 |
| 12 | 29.7 | 7.5 |

In some embodiments of the present invention, the crystalline Form B of the compound of Formula I has an X-ray powder diffraction pattern substantially as shown in FIG. 3.

Without limitation, the present invention provides a typical example of a differential scanning calorimetry (DSC) measurement pattern of the crystalline Form B of the compound of Formula I, the heat flow from the sample is plotted as a function of temperature in the DSC pattern, and the rate of temperature change is about 10° C./min. The DSC pattern is characterized in that it has an absorption peak at about 224.7° C.

In another aspect, the present invention provides a process for preparing the crystalline Form B of the compound of Formula I, comprising: dissolving the compound of Formula I in ethyl acetate at room temperature to obtain a clear solution, concentrating the solution under reduced pressure and drying to obtain the crystalline Form B of the compound of Formula I.

In some embodiments of the above preparation process, the molar volume ratio of the compound of Formula I to ethyl acetate is 1 mmol: 2 to 10 mL, or 1 mmol: 2 to 5 mL.

The present invention also relates to an acid addition salt of the compound of Formula I, and a hydrate and a solvate of the acid addition salt, and the acid is selected from the group consisting of an organic acid and an inorganic acid. In some embodiments, the organic acid is selected from the group consisting of methanesulfonic acid, ethanesulfonic acid, p-toluenesulfonic acid, maleic acid, oxalic acid, citric acid, malonic acid, acetic acid, benzoic acid, glutaric acid, D-tartaric acid, L-tartaric acid and fumaric acid. In some embodiments, the inorganic acid is selected from the group consisting of hydrochloric acid, hydrobromic acid, sulfuric acid, and phosphoric acid. In some embodiments, the acid is selected from the group consisting of methanesulfonic acid, p-toluenesulfonic acid, maleic acid, hydrochloric acid, and sulfuric acid; in some embodiments, the acid is selected from the group consisting of methanesulfonic acid, p-toluenesulfonic acid, and hydrochloric acid.

In still another aspect, the present invention provides a mesylate of the compound of Formula I, or a hydrate or solvate thereof. Optionally, the mesylate of the compound of Formula I, or the hydrate or solvate thereof is in crystalline form or amorphous form.

In a further aspect, the present invention provides a p-toluenesulfonate of the compound of Formula I, or a hydrate or solvate thereof. Optionally, the p-toluenesulfonate of the compound of Formula I, or the hydrate or solvate thereof is in crystalline form or amorphous form.

In still another aspect, the present invention provides a maleate of the compound of Formula I, or a hydrate or solvate thereof. Optionally, the maleate of the compound of Formula I, or the hydrate or solvate thereof is in crystalline form or amorphous form.

In yet another aspect, the present invention provides a hydrochloride salt of the compound of Formula I, or a hydrate or solvate thereof. Optionally, the hydrochloride salt of the compound of Formula I, or the hydrate or solvate thereof is in crystalline form or amorphous form.

In another aspect, the present invention provides a sulfate of the compound of Formula I, or a hydrate or solvate thereof. Optionally, the sulfate of the compound of Formula I, or the hydrate or solvate thereof is in crystalline form or amorphous form.

For example, the mesylate of the compound of Formula I provided in the present invention may be in crystalline form or amorphous form, the hydrate of the mesylate of the compound of Formula I provided in the present invention may be in crystalline form or amorphous form, and the solvate of the mesylate of the compound of Formula I provided in the present invention may be in crystalline form or amorphous form.

In a further aspect, the present invention provides a process for preparing an acid addition salt of the compound of Formula I, comprising the steps of: dissolving the compound of Formula I in an organic solvent; adding an acid under stirring; after 0.5 to 2 hours, precipitating a solid from the reaction solution; and then filtering and drying the solid to obtain the acid addition salt of the compound of Formula I, or a hydrate or solvate thereof.

In some embodiments of the above process for preparing the acid addition salt of the compound of Formula I, the organic solvent is selected from the group consisting of methanol, ethanol, isopropanol, tert-butanol, ethyl acetate, acetone, methyl tert-butyl ether, ethylene glycol dimethyl ether, tetrahydrofuran and acetonitrile, and mixed solvents of more than one solvent selected from the above-mentioned solvents in any ratio. In some embodiments, the organic solvent is selected from the group consisting of ethyl acetate, acetone, acetonitrile, methyl tert-butyl ether, and mixed solvents thereof.

In some embodiments of the above process for preparing the acid addition salt of the compound of Formula I, the molar ratio of the compound of Formula I to the acid is 1:0.9 to 5, or 1:0.9 to 3.

In some embodiments of the above process for preparing the acid addition salt of the compound of Formula I, the molar volume ratio of the compound of Formula I to the organic solvent is 1 mmol: 1 to 20 mL, or 1 mmol: 1 to 15 mL.

In some embodiments of the above process for preparing the acid addition salt of the compound of Formula I, the following operations in the process for preparing the acid addition salt of the compound of Formula I may be carried out at 0 to 50° C.: dissolving the compound of Formula I in the organic solvent, and adding the acid under stirring to react for 0.5 to 2 hours; the above operations may be also carried out at the reflux temperature of the organic solvent. In some embodiments, the following operations in the process for preparing the acid addition salt of the compound of Formula I are carried out at 20 to 30° C. or the reflux temperature of the organic solvent: dissolving the compound of Formula I in the organic solvent, and adding the acid under stirring to react for 0.5 to 2 hours.

In some embodiments of the above process for preparing the acid addition salt of the compound of Formula I, the acid may be added directly to the reaction system or may be pre-formulated into a solution to be added to the reaction system. The solvent for the preformulation includes, but is not limited to, water, methanol, ethanol, acetone, tetrahydrofuran and acetonitrile, and mixed solvents of more than one solvent selected from the above-mentioned solvents in any ratio; the solvent for the preformulation may be the same as or different from the organic solvent used to dissolve the compound of Formula I. The molar volume ratio of the acid to the solvent for the preformulation is 1 mmol: 0.1 to 1 mL, or 1 mmol: 0.3 to 1 mL.

It should be noted that, in the present invention, the compound of Formula I may form a hemi-, mono- or di-salt by the addition reaction with 0.5 molecule, 1 molecule or 2 molecules of an acid, respectively, based on the nature of the acid and the preparation conditions.

In some embodiments of the above process for preparing the acid addition salt of the compound of Formula I, the acid added in the preparation may be in the form of a free acid or a hydrate of the acid.

In some embodiments of the above process for preparing the acid addition salt of the compound of Formula I, the acid addition salt of the compound of Formula I, or the hydrate or solvate thereof obtained by the preparation process is optionally in crystalline form or amorphous form.

The present invention also relates to a crystal of the mesylate of the compound of Formula I.

In an aspect, the present invention provides a crystalline Form I of the mesylate of the compound of Formula I, characterized in that an X-ray powder diffraction spectrum thereof has diffraction peaks expressed by 2θ values at about 6.2°, 12.1°, 20.2° and 25.0°; typically has diffraction peaks expressed by 2θ values at about 6.2°, 12.1°, 18.3°, 20.2°, 22.7°, 24.6° and 25.0°; more typically has diffraction peaks expressed by 2θ values at about 6.2°, 12.1°, 17.8°, 18.3°, 20.2°, 21.2°, 22.7°, 23.6°, 24.6°, 25.0° and 27.0°; and even more typically has diffraction peaks expressed by 2θ values at about 6.2°, 12.1°, 13.0°, 13.9°, 17.8°, 18.3°, 20.2°, 21.2°, 22.7°, 23.6°, 24.6°, 25.0° and 27.0°.

As an embodiment of the present invention, the peak positions and intensities of the characteristic peaks in the X-ray powder diffraction spectrum of the crystalline Form I of the mesylate of the compound of Formula I according to the present invention have the characteristics shown in Table 3:

TABLE 3

| No. | 2θ(°) | Relative Intensity(I/I$_0$) |
| --- | --- | --- |
| 1 | 6.2 | 100.0 |
| 2 | 12.1 | 63.2 |
| 3 | 13.0 | 9.6 |
| 4 | 13.9 | 9.2 |
| 5 | 17.8 | 12.6 |
| 6 | 18.3 | 20.9 |
| 7 | 20.2 | 96.3 |
| 8 | 21.2 | 17.4 |
| 9 | 22.7 | 25.6 |
| 10 | 23.6 | 19.3 |
| 11 | 24.6 | 32.3 |
| 12 | 25.0 | 40.0 |
| 13 | 27.0 | 18.7 |

In some embodiments of the present invention, the crystalline Form I of the mesylate of the compound of Formula I has an X-ray powder diffraction pattern substantially as shown in FIG. 5.

Without limitation, the present invention provides a typical example of a differential scanning calorimetry (DSC) measurement pattern of the crystalline Form I of the mesylate of the compound of Formula I, the heat flow from the sample is plotted as a function of temperature in the DSC pattern, and the rate of temperature change is about 10° C./min. The DSC pattern is characterized in that it has an absorption peak at about 147.3° C.

In another aspect, the present invention provides a process for preparing the above crystalline Form I of the mesylate of the compound of Formula I, comprising the steps of:

(i) dissolving the compound of Formula I in methyl tert-butyl ether;

(ii) adding methanesulfonic acid dropwise into the solution of step (i) at room temperature; and (iii) precipitating a solid, filtering and drying the solid.

In some embodiments of the above process for preparing the crystalline Form I of the mesylate of the compound of Formula I, the molar volume ratio of the compound of Formula I to methyl tert-butyl ether in step (i) is 1 mmol: 10 to 20 mL, or 1 mmol: 10 to 15 mL.

In some embodiments of the above process for preparing the crystalline Form I of the mesylate of the compound of Formula I, the molar ratio of the compound of Formula I to methanesulfonic acid is 1:1 to 1.5, or 1:1 to 1.2.

In another aspect, the present invention provides a crystalline Form II of the mesylate of the compound of Formula I, characterized in that an X-ray powder diffraction spectrum thereof has diffraction peaks expressed by 2θ values at about 7.3°, 14.2°, 19.2°, 21.1°, 21.5° and 25.3°; typically has diffraction peaks expressed by 2θ values at about 7.3°, 9.7°, 10.6°, 14.2°, 19.2°, 19.5°, 19.9°, 20.4°, 21.1°, 21.5°, 22.4° and 25.3°; more typically has diffraction peaks expressed by 2θ values at about 7.3°, 9.7°, 10.6°, 11.6°, 14.2°, 16.4°, 18.9°, 19.2°, 19.5°, 19.9°, 20.4°, 21.1°, 21.5°, 22.0°, 22.4°, 24.2°, 24.7°, 25.3° and 27.5°; and even more typically has diffraction peaks expressed by 2θ values at about 7.3°, 9.7°, 10.6°, 11.6°, 13.2°, 14.2°, 16.4°, 17.2°, 18.9°, 19.2°, 19.5°, 19.9°, 20.4°, 21.1°, 21.5°, 22.0°, 22.4°, 23.0°, 23.2°, 24.2°, 24.7°, 25.3° and 27.5°.

As an embodiment of the present invention, the peak positions and intensities of the characteristic peaks in the X-ray powder diffraction spectrum of the crystalline Form II of the mesylate of the compound of Formula I according to the present invention have the characteristics shown in Table 4:

TABLE 4

| No. | 2θ(°) | Relative Intensity(I/I₀) |
| --- | --- | --- |
| 1 | 7.3 | 100.0 |
| 2 | 9.7 | 19.2 |
| 3 | 10.6 | 20.2 |
| 4 | 11.6 | 3.9 |
| 5 | 13.2 | 6.8 |
| 6 | 14.2 | 27.7 |
| 7 | 16.4 | 8.7 |
| 8 | 17.2 | 10.5 |
| 9 | 18.9 | 15.6 |
| 10 | 19.2 | 58.1 |
| 11 | 19.5 | 22.6 |
| 12 | 19.9 | 23.5 |
| 13 | 20.4 | 25.5 |

TABLE 4-continued

| No. | 2θ(°) | Relative Intensity(I/I₀) |
| --- | --- | --- |
| 14 | 21.1 | 31.9 |
| 15 | 21.5 | 70.7 |
| 16 | 22.0 | 11.3 |
| 17 | 22.4 | 24.6 |
| 18 | 23.0 | 10.1 |
| 19 | 23.2 | 8.0 |
| 20 | 24.2 | 15.4 |
| 21 | 24.7 | 11.4 |
| 22 | 25.3 | 45.5 |
| 23 | 27.5 | 14.8 |

In some embodiments of the present invention, the crystalline Form II of the mesylate of the compound of Formula I has an X-ray powder diffraction pattern substantially as shown in FIG. 7.

Without limitation, the present invention provides a typical example of a differential scanning calorimetry (DSC) measurement pattern of the crystalline Form II of the mesylate of the compound of Formula I, the heat flow from the sample is plotted as a function of temperature in the DSC pattern, and the rate of temperature change is about 10° C./min. The DSC pattern is characterized in that it has an absorption peak at about 192.8° C.

In a further aspect, the present invention provides a process for preparing the above crystalline Form II of the mesylate of the compound of Formula I, comprising the steps of:

(i) dissolving the compound of Formula I in methyl tert-butyl ether;

(ii) adding methanesulfonic acid dropwise into the solution of step (i) at a reflux temperature;

(iii) cooling the solution of step (ii) to room temperature to precipitate a solid; and (iv) filtering and drying the solid.

In some embodiments of the above process for preparing the crystalline Form II of the mesylate of the compound of Formula I, the molar volume ratio of the compound of Formula I to methyl tert-butyl ether in step (i) is 1 mmol: 10 to 20 mL, or 1 mmol: 10 to 15 mL.

In some embodiments of the above process for preparing the crystalline Form II of the mesylate of the compound of Formula I, the reflux temperature in step (ii) is 50 to 60° C., or 55 to 60° C.

In some embodiments of the above process for preparing the crystalline Form II of the mesylate of the compound of Formula I, the molar ratio of the compound of Formula I to methanesulfonic acid is 1:1 to 1.5, or 1:1 to 1.2.

In still another aspect, the present invention provides a crystalline Form III of the mesylate of the compound of Formula I, characterized in that an X-ray powder diffraction spectrum thereof has diffraction peaks expressed by 2θ values at about 8.2°, 8.5°, 8.7°, 8.8°, 16.2°, 18.1°, 18.6°, 19.8° and 22.2°; typically has diffraction peaks expressed by 2θ values at about 6.8°, 8.2°, 8.5°, 8.7°, 8.8°, 16.2°, 18.1°, 18.6°, 19.8°, 21.0°, 21.4° and 22.2°; more typically has diffraction peaks expressed by 2θ values at about 6.8°, 8.2°, 8.5°, 8.7°, 8.8°, 16.2°, 16.6°, 17.0°, 18.1°, 18.6°, 19.8°, 20.1°, 21.0°, 21.4°, 22.2°, 22.8°, 23.6° and 25.9°; and even more typically has diffraction peaks expressed by 2θ values at about 6.8°, 8.2°, 8.5°, 8.7°, 8.8°, 16.2°, 16.6°, 17.0°, 17.3°, 18.1°, 18.6°, 18.8°, 19.2°, 19.8°, 20.1°, 20.4°, 21.0°, 21.4°, 22.2°, 22.8°, 23.6°, 24.6°, 25.9° and 27.7°.

As an embodiment of the present invention, the peak positions and intensities of the characteristic peaks in the X-ray powder diffraction spectrum of the crystalline Form III of the mesylate of the compound of Formula I according to the present invention have the characteristics shown in Table 5:

TABLE 5

| No. | 2θ(°) | Relative Intensity(I/I$_0$) |
|---|---|---|
| 1 | 6.8 | 25.2 |
| 2 | 8.2 | 100.0 |
| 3 | 8.5 | 73.1 |
| 4 | 8.7 | 46.0 |
| 5 | 8.8 | 50.1 |
| 6 | 16.2 | 30.8 |
| 7 | 16.6 | 14.6 |
| 8 | 17.0 | 13.9 |
| 9 | 17.3 | 12.0 |
| 10 | 18.1 | 38.4 |
| 11 | 18.6 | 39.1 |
| 12 | 18.8 | 18.3 |
| 13 | 19.2 | 13.4 |
| 14 | 19.8 | 32.2 |
| 15 | 20.1 | 21.7 |
| 16 | 20.4 | 11.4 |
| 17 | 21.0 | 24.8 |
| 18 | 21.4 | 31.4 |
| 19 | 22.2 | 32.9 |
| 20 | 22.8 | 14.2 |
| 21 | 23.6 | 14.0 |
| 22 | 24.6 | 11.2 |
| 23 | 25.9 | 16.9 |
| 24 | 27.7 | 12.6 |

In some embodiments of the present invention, the crystalline Form III of the mesylate of the compound of Formula I has an X-ray powder diffraction pattern substantially as shown in FIG. 9.

Without limitation, the present invention provides a typical example of a differential scanning calorimetry (DSC) measurement pattern of the crystalline Form III of the mesylate of the compound of Formula I, the heat flow from the sample is plotted as a function of temperature in the DSC pattern, and the rate of temperature change is about 10° C./min. The DSC pattern is characterized in that it has absorption peaks at about 110.5° C. and 166.0° C.

In a further aspect, the present invention provides a process for preparing the above crystalline Form III of the mesylate of the compound of Formula I, comprising the steps of:
(i) dissolving the compound of Formula I in ethyl acetate;
(ii) adding methanesulfonic acid dropwise into the solution of step (i) at room temperature; and
(iii) precipitating a solid, filtering and drying the solid.

In some embodiments of the above process for preparing the crystalline Form III of the mesylate of the compound of Formula I, the molar volume ratio of the compound of Formula I to ethyl acetate in step (i) is 1 mmol: 5 to 15 mL, or 1 mmol: 5 to 10 mL.

In some embodiments of the above process for preparing the crystalline Form III of the mesylate of the compound of Formula I, the molar ratio of the compound of Formula I to methanesulfonic acid is 1:1 to 1.5, or 1:1 to 1.2.

In yet another aspect, the present invention provides a crystalline Form IV of the mesylate of the compound of Formula I, characterized in that an X-ray powder diffraction spectrum thereof has diffraction peaks expressed by 2θ values at about 8.0°, 8.4°, 15.8°, 20.2°, 21.2° and 23.7°; typically has diffraction peaks expressed by 2θ values at about 8.0°, 8.4°, 8.8°, 15.8°, 17.9°, 19.8°, 20.2°, 21.2° and 23.7°; more typically has diffraction peaks expressed by 2θ values at about 8.0°, 8.4°, 8.8°, 12.0°, 15.8°, 16.6°, 17.9°, 19.8°, 20.2°, 21.2°, 23.7°, 24.2° and 25.2°; and even more typically has diffraction peaks expressed by 2θ values at about 8.0°, 8.4°, 8.8°, 12.0°, 13.6°, 15.8°, 16.6°, 17.9°, 19.8°, 20.2°, 21.2°, 23.7°, 24.2°, 25.2°, 26.2°, 26.7° and 29.5°.

As an embodiment of the present invention, the peak positions and intensities of the characteristic peaks in the X-ray powder diffraction spectrum of the crystalline Form IV of the mesylate of the compound of Formula I according to the present invention have the characteristics shown in Table 6:

TABLE 6

| No. | 2θ(°) | Relative Intensity(I/I$_0$) |
|---|---|---|
| 1 | 8.0 | 100.0 |
| 2 | 8.4 | 29.7 |
| 3 | 8.8 | 17.1 |
| 4 | 12.0 | 13.2 |
| 5 | 13.6 | 8.5 |
| 6 | 15.8 | 29.8 |
| 7 | 16.6 | 10.4 |
| 8 | 17.9 | 18.8 |
| 9 | 19.8 | 24.4 |
| 10 | 20.2 | 26.9 |
| 11 | 21.2 | 33.6 |
| 12 | 23.7 | 26.7 |
| 13 | 24.2 | 13.3 |
| 14 | 25.2 | 11.5 |
| 15 | 26.2 | 10.7 |
| 16 | 26.7 | 10.2 |
| 17 | 29.5 | 9.8 |

In some embodiments of the present invention, the crystalline Form IV of the mesylate of the compound of Formula I has an X-ray powder diffraction pattern substantially as shown in FIG. 11.

Without limitation, the present invention provides a typical example of a differential scanning calorimetry (DSC) measurement pattern of the crystalline Form IV of the mesylate of the compound of Formula I, the heat flow from the sample is plotted as a function of temperature in the DSC pattern, and the rate of temperature change is about 10° C./min. The DSC pattern is characterized in that it has absorption peaks at about 94.4° C. and 166.0° C.

In another aspect, the present invention provides a process for preparing the above crystalline Form IV of the mesylate of the compound of Formula I, comprising the steps of:
(i) dissolving the compound of Formula I in ethyl acetate;
(ii) adding methanesulfonic acid dropwise into the solution of step (i) at room temperature;
(iii) precipitating a solid, filtering and drying the solid; and
(iv) further drying the solid of step (iii) under vacuum at 100-110° C.

In some embodiments of the above process for preparing the crystalline Form IV of the mesylate of the compound of Formula I, the molar volume ratio of the compound of Formula I to ethyl acetate in step (i) is 1 mmol: 5 to 15 mL, or 1 mmol: 5 to 10 mL.

In some embodiments of the above process for preparing the crystalline Form IV of the mesylate of the compound of Formula I, the molar ratio of the compound of Formula I to methanesulfonic acid is 1:1 to 3.5, or 1:1 to 3.

In another aspect, the present invention provides a crystalline Form V of the mesylate of the compound of Formula I, characterized in that an X-ray powder diffraction spectrum thereof has diffraction peaks expressed by 2θ values at about 8.1°, 8.2°, 8.5°, 8.7°, 16.1°, 18.5° and 19.8°; typically has diffraction peaks expressed by 2θ values at about 6.8°, 8.1°, 8.2°, 8.5°, 8.7°, 16.1°, 17.3°, 18.5°, 19.8°, 21.0° and 22.2°; more typically has diffraction peaks expressed by 2θ values at about 6.8°, 8.1°, 8.2°, 8.5°, 8.7°, 15.8°, 16.1°, 17.3°, 18.5°, 19.8°, 20.1°, 21.0°, 22.2°, 23.6°, 24.6° and 27.7°; and even more typically has diffraction peaks expressed by 2θ values at about 6.8°, 8.1°, 8.2°, 8.5°, 8.7°, 15.8°, 16.1°, 16.7°, 17.3°, 18.1°, 18.5°, 19.8°, 20.1°, 20.3°, 21.0°, 21.4°, 22.2°, 22.8°, 23.6°, 24.3°, 24.6° and 27.7°.

As an embodiment of the present invention, the peak positions and intensities of the characteristic peaks in the X-ray powder diffraction spectrum of the crystalline Form V of the mesylate of the compound of Formula I according to the present invention have the characteristics shown in Table 7:

TABLE 7

| No. | 2θ(°) | Relative Intensity(I/I$_0$) |
| --- | --- | --- |
| 1 | 6.8 | 30.1 |
| 2 | 8.1 | 100.0 |
| 3 | 8.2 | 92.1 |
| 4 | 8.5 | 40.1 |
| 5 | 8.7 | 42.0 |
| 6 | 15.8 | 20.1 |
| 7 | 16.1 | 39.6 |
| 8 | 16.7 | 12.1 |
| 9 | 17.3 | 25.1 |
| 10 | 18.1 | 13.9 |
| 11 | 18.5 | 54.8 |
| 12 | 19.8 | 51.7 |
| 13 | 20.1 | 20.0 |
| 14 | 20.3 | 14.3 |
| 15 | 21.0 | 24.4 |
| 16 | 21.4 | 17.6 |
| 17 | 22.2 | 35.2 |
| 18 | 22.8 | 10.1 |
| 19 | 23.6 | 19.8 |
| 20 | 24.3 | 10.6 |
| 21 | 24.6 | 17.4 |
| 22 | 27.7 | 18.0 |

In some embodiments of the present invention, the crystalline Form V of the mesylate of the compound of Formula I has an X-ray powder diffraction pattern substantially as shown in FIG. 13.

Without limitation, the present invention provides a typical example of a differential scanning calorimetry (DSC) measurement pattern of the crystalline Form V of the mesylate of the compound of Formula I, the heat flow from the sample is plotted as a function of temperature in the DSC pattern, and the rate of temperature change is about 10° C./min. The DSC pattern is characterized in that it has absorption peaks at about 116.6° C. and 165.8° C.

In a further aspect, the present invention provides a process for preparing the above crystalline Form V of the mesylate of the compound of Formula I, comprising the steps of:
(i) dissolving the compound of Formula I in acetone;
(ii) adding methanesulfonic acid dropwise into the solution of step (i) at room temperature; and
(iii) precipitating a solid, filtering and drying the solid.

In some embodiments of the above process for preparing the crystalline Form V of the mesylate of the compound of Formula I, the molar volume ratio of the compound of Formula I to acetone in step (i) is 1 mmol: 5 to 15 mL, or 1 mmol: 5 to 10 mL.

In some embodiments of the above process for preparing the crystalline Form V of the mesylate of the compound of Formula I, the molar ratio of the compound of Formula I to methanesulfonic acid is 1:1 to 3.5, or 1:1 to 3.

In still another aspect, the present invention provides a crystalline Form VI of the mesylate of the compound of Formula I, characterized in that an X-ray powder diffraction spectrum thereof has diffraction peaks expressed by 2θ values at about 8.5°, 16.7°, 18.1° and 22.8°; typically has diffraction peaks expressed by 2θ values at about 6.3°, 8.5°, 16.7°, 18.1°, 20.1°, 20.5°, 21.4°, 22.8° and 25.9°; and more typically has diffraction peaks expressed by 2θ values at about 6.3°, 8.5°, 16.7°, 17.0°, 18.1°, 19.3°, 20.1°, 20.5°, 21.4°, 22.8°, 25.9° and 26.2°.

As an embodiment of the present invention, the peak positions and intensities of the characteristic peaks in the X-ray powder diffraction spectrum of the crystalline Form VI of the mesylate of the compound of Formula I according to the present invention have the characteristics shown in Table 8:

TABLE 8

| No. | 2θ(°) | Relative Intensity(I/I$_0$) |
| --- | --- | --- |
| 1 | 6.3 | 6.8 |
| 2 | 8.5 | 100.0 |
| 3 | 16.7 | 25.7 |
| 4 | 17.0 | 13.4 |
| 5 | 18.1 | 16.7 |
| 6 | 19.3 | 9.2 |
| 7 | 20.1 | 11.6 |
| 8 | 20.5 | 10.9 |
| 9 | 21.4 | 15.1 |
| 10 | 22.8 | 21.5 |
| 11 | 25.9 | 11.4 |
| 12 | 26.2 | 9.0 |

In some embodiments of the present invention, the crystalline Form VI of the mesylate of the compound of Formula I has an X-ray powder diffraction pattern substantially as shown in FIG. 15.

Without limitation, the present invention provides a typical example of a differential scanning calorimetry (DSC) measurement pattern of the crystalline Form VI of the mesylate of the compound of Formula I, the heat flow from the sample is plotted as a function of temperature in the DSC pattern, and the rate of temperature change is about 10° C./min. The DSC pattern is characterized in that it has absorption peaks at about 103.5° C. and 154.2° C.

In a further aspect, the present invention provides a process for preparing the above crystalline Form VI of the mesylate of the compound of Formula I, comprising the steps of:
(i) dissolving the compound of Formula I in acetonitrile;
(ii) adding methanesulfonic acid dropwise into the solution of step (i) at room temperature; and
(iii) precipitating a solid, filtering and drying the solid;
wherein, the molar ratio of the compound of Formula I to methanesulfonic acid is 1:1 to 1.5, or 1:1 to 1.2.

In some embodiments of the above process for preparing the crystalline Form VI of the mesylate of the compound of Formula I, the molar volume ratio of the compound of Formula I to acetonitrile in step (i) is 1 mmol: 5 to 15 mL, or 1 mmol: 5 to 10 mL.

In yet another aspect, the present invention provides a crystalline Form VII of the mesylate of the compound of Formula I, characterized in that an X-ray powder diffraction spectrum thereof has diffraction peaks expressed by 2θ values at about 8.2°, 16.1°, 18.5°, 19.7° and 22.1°; typically has diffraction peaks expressed by 2θ values at about 6.8°, 8.2°, 16.1°, 18.5°, 19.7°, 21.0°, 22.1°, 23.6°, 24.6° and 27.6°; more typically has diffraction peaks expressed by 2θ values at about 6.8°, 8.2°, 8.7°, 16.1°, 17.2°, 18.1°, 18.5°, 18.8°, 19.7°, 21.0°, 22.1°, 23.6°, 24.6° and 27.6°; and even more typically has diffraction peaks expressed by 2θ values at about 6.8°, 8.2°, 8.7°, 16.1°, 17.2°, 18.1°, 18.5°, 18.8°, 19.7°, 21.0°, 22.1°, 22.8°, 23.6°, 24.3°, 24.6°, 27.6° and 28.8°.

As an embodiment of the present invention, the peak positions and intensities of the characteristic peaks in the X-ray powder diffraction spectrum of the crystalline Form VII of the mesylate of the compound of Formula I according to the present invention have the characteristics shown in Table 9:

TABLE 9

| No. | 2θ(°) | Relative Intensity(I/I$_0$) |
| --- | --- | --- |
| 1 | 6.8 | 25.7 |
| 2 | 8.2 | 100.0 |
| 3 | 8.7 | 13.7 |
| 4 | 16.1 | 46.9 |
| 6 | 17.2 | 15.9 |
| 7 | 18.1 | 14.4 |
| 8 | 18.5 | 57.3 |
| 9 | 18.8 | 17.3 |
| 10 | 19.7 | 57.9 |
| 11 | 21.0 | 28.1 |
| 12 | 22.1 | 59.1 |
| 13 | 22.8 | 9.8 |
| 14 | 23.6 | 26.3 |
| 15 | 24.3 | 13.6 |
| 16 | 24.6 | 26.3 |
| 17 | 27.6 | 28.1 |
| 18 | 28.8 | 9.7 |

In some embodiments of the present invention, the crystalline Form VII of the mesylate of the compound of Formula I has an X-ray powder diffraction pattern substantially as shown in FIG. 17.

Without limitation, the present invention provides a typical example of a differential scanning calorimetry (DSC) measurement pattern of the crystalline Form VII of the mesylate of the compound of Formula I, the heat flow from the sample is plotted as a function of temperature in the DSC pattern, and the rate of temperature change is about 10° C./min. The DSC pattern is characterized in that it has absorption peaks at about 110.0° C. and 166.1° C.

In a further aspect, the present invention provides a process for preparing the above crystalline Form VII of the mesylate of the compound of Formula I, comprising the steps of:

(i) dissolving the compound of Formula I in acetonitrile;

(ii) adding methanesulfonic acid dropwise into the solution of step (i) at room temperature; and (iii) precipitating a solid, filtering and drying the solid;

wherein, the molar ratio of the compound of Formula I to methanesulfonic acid is 1:2 to 3.5, or 1:2 to 3.

In some embodiments of the above process for preparing the crystalline Form VII of the mesylate of the compound of Formula I, the molar volume ratio of the compound of Formula I to acetonitrile in step (i) is 1 mmol: 5 to 15 mL, or 1 mmol: 5 to 10 mL.

In yet another aspect, the present invention provides a crystalline Form VIII of the mesylate of the compound of Formula I, characterized in that an X-ray powder diffraction spectrum thereof has diffraction peaks expressed by 2θ values at about 7.12°, 14.05°, 19.11°, 21.02°, 21.33° and 25.15°; typically has diffraction peaks expressed by 2θ values at about 7.12°, 9.60°, 10.46°, 14.05°, 18.80°, 19.11°, 19.41°, 19.80°, 20.24°, 21.02°, 21.33°, 22.32°, 24.12° and 25.15°; and more typically has diffraction peaks expressed by 2θ values at about 7.12°, 9.60°, 10.46°, 13.07°, 14.05°, 16.20°, 17.10°, 18.80°, 19.11°, 19.41°, 19.80°, 20.24°, 21.02°, 21.33°, 21.92°, 22.32°, 22.89°, 23.11°, 24.12°, 24.56°, 25.15°, 27.42° and 30.21°.

As an embodiment of the present invention, the peak positions and intensities of the characteristic peaks in the X-ray powder diffraction spectrum of the crystalline Form VIII of the mesylate of the compound of Formula I according to the present invention have the characteristics shown in Table 10:

TABLE 10

| No. | 2θ(°) | Relative Intensity(I/I$_0$) |
| --- | --- | --- |
| 1 | 7.12 | 100.0 |
| 2 | 9.60 | 10.4 |
| 3 | 10.46 | 12.2 |
| 4 | 13.07 | 4.5 |
| 5 | 14.05 | 26.1 |
| 6 | 16.20 | 6.7 |
| 7 | 17.10 | 6.1 |
| 8 | 18.80 | 10.7 |
| 9 | 19.11 | 33.2 |
| 10 | 19.41 | 14.0 |
| 11 | 19.80 | 15.6 |
| 12 | 20.24 | 13.0 |
| 13 | 21.02 | 27.9 |
| 14 | 21.33 | 43.4 |
| 15 | 21.92 | 7.2 |
| 16 | 22.32 | 19.2 |
| 17 | 22.89 | 5.3 |
| 18 | 23.11 | 5.0 |
| 19 | 24.12 | 11.2 |
| 20 | 24.56 | 8.8 |
| 21 | 25.15 | 31.4 |
| 22 | 27.42 | 8.8 |
| 23 | 30.21 | 5.1 |

In some embodiments of the present invention, the crystalline Form VIII of the mesylate of the compound of Formula I has an X-ray powder diffraction pattern substantially as shown in FIG. 19.

In a further aspect, the present invention provides a process for preparing the above crystalline Form VIII of the mesylate of the compound of Formula I, comprising the steps of:

(i) dissolving the compound of Formula I in methyl tert-butyl ether;

(ii) adding a solution of methanesulfonic acid in methyl tert-butyl ether dropwise into the solution of step (i) at a reflux temperature;

(iii) cooling the solution of step (ii) to room temperature to precipitate a solid; and (iv) filtering and drying the solid.

In some embodiments of the above process for preparing the crystalline Form VIII of the mesylate of the compound of Formula I, the molar volume ratio of the compound of Formula I to methyl tert-butyl ether in step (i) is 1 mmol: 10 to 20 mL, or 1 mmol: 10 to 15 mL.

In some embodiments of the above process for preparing the crystalline Form VIII of the mesylate of the compound of Formula I, the reflux temperature in step (ii) is 50 to 60° C., or 55 to 60° C.

In some embodiments of the above process for preparing the crystalline Form VIII of the mesylate of the compound of Formula I, the molar volume ratio of methanesulfonic acid to methyl tert-butyl ether in the step (ii) is 1 mmol: 5 to 10 mL, or 1 mmol: 8 to 10 mL.

In some embodiments of the above process for preparing the crystalline Form VIII of the mesylate of the compound of Formula I, the molar ratio of the compound of Formula I to methanesulfonic acid is 1:0.5 to 1.5, or 1:0.5 to 1.0.

In some embodiments of the above process for preparing the crystalline Form VIII of the mesylate of the compound of Formula I, the reflux time is 0.5 to 2 hours, or 1 to 1.5 hours.

The crystalline Forms A and B of the compound of Formula I, the salts of the compound of Formula I and the crystals thereof (including the crystalline Forms I, II, III, IV, V, VI, VII and VIII of the mesylate of the compound of Formula I) have high stability, low hygroscopicity, good in vivo metabolic level, and long half-life, and they have a good inhibiting activity against IDH2, have good properties in terms of physical properties, safety and metabolic stability, and have a high value as a drug.

In some embodiments, the crystals of the compound of Formula I, the acid addition salts of the compound of Formula I and the hydrates or solvates thereof, and the crystals of the mesylate of the compound of Formula I obtained by the above various preparation methods of the present invention may be dried by routine methods in the field. In some embodiments, the drying method comprises drying at room temperature, drying under reduced pressure and blast drying. In some embodiments, the drying method is vacuum drying under reduced pressure. In some embodiments, the drying device is a fume hood, a vacuum oven, or a blast oven. In some embodiments, the drying temperature is 60° C. to 100° C., 80° C. to 100° C., or 90° C. to 100° C. In some embodiments, the drying time is 2 to 10 hours, 2 to 8 hours, or 4 to 8 hours.

In the present invention, a solid may be precipitated from the reaction solution in such a manner that the precipitation spontaneously occurs in the solvent system; alternatively, the precipitation may be induced by reducing the temperature of the reaction solution, especially in the case that the initial temperature of the reaction solution is elevated; alternatively, the precipitation may also be induced by reducing the solvent volume (e.g. under reduced pressure), or by completely evaporating the solvent; alternatively, the precipitation may be caused by adding an antisolvent; alternatively, the precipitation may be initiated by adding crystallization seeds. For example, in the preparation process of the hydrochloride salt of the compound of Formula I, a solid is precipitated from the reaction solution in such a manner that the precipitation spontaneously occurs in the solvent system.

In the present invention, "crystal" refers to a solid having a highly regular chemical structure. The crystals in the present invention are in a form that has at least a specific weight percentage of the crystal. The specific percentage is 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9% or any percentage between 10% and 99.9%. In some embodiments, the specific percentage is 50%, 60%, 70%, 75%, 80%, 85%, 87%, 88%, 89%, 90%, 91%, 92%, 93%, 94%, 95%, 96%, 97%, 98%, 99%, 99.5%, 99.9% or any percentage between 50% and 99.9%. In some embodiments, the specific percentage is 80%, 85%, 87%, 88%, 89%, 90%, 91%, 92%, 93%, 94%, 95%, 96%, 97%, 98%, 99%, 99.5%, 99.9%, or any percentage between 80% and 99.9%. In some embodiments, the specific percentage is 90%, 91%, 92%, 93%, 94%, 95%, 96%, 97%, 98%, 99%, 99.5%, 99.9% or any percentage between 90% and 99.9%.

The present invention provides a pharmaceutical composition comprising a therapeutically effective amount of a crystal of the compound of Formula I, and a pharmaceutically acceptable carrier or other excipient(s); or comprising a therapeutically effective amount of an acid addition salt of the compound of Formula I, or a hydrate or solvate thereof, and a pharmaceutically acceptable carrier or other excipient (s); or comprising a crystal of the mesylate of the compound of Formula I, and a pharmaceutically acceptable carrier or other excipient(s). The crystal of the compound of Formula I is the crystalline Form A or B of the compound of Formula I; the acid addition salt of the compound of Formula I is a mesylate of the compound of Formula I, a hydrochloride salt of the compound of Formula I, a sulfate of the compound of Formula I, a p-toluenesulfonate of the compound of Formula I, or a maleate of the compound of Formula I, or a hydrate or solvate of the above-mentioned addition salts, the above-mentioned addition salts or the hydrates or solvates thereof are optionally in crystalline form or amorphous form; and the crystal of the mesylate of the compound of Formula I includes the crystalline Forms I, II, III, IV, V, VI, VII and VIII. The pharmaceutically acceptable carrier may be a solid or liquid. The solid carrier may comprise one or more of flavoring agents, lubricants, solubilizers, suspending agents, fillers, binders, tablet disintegrating agents or encapsulating materials. Suitable solid carriers include, for example, magnesium stearate, talc, sucrose, lactose, dextrin, starch, gelatin, cellulose, methylcellulose, sodium carboxymethylcellulose and polyvinylpyrrolidone. The liquid carriers are used to prepare compositions such as solutions, suspensions, emulsions, syrups and the like. Suitable liquid carriers for oral and parenteral administration include water, alcohols, oil and the like.

The pharmaceutical composition may be made into certain dosage forms. Administration routes are preferably oral administration, parenteral administration (including subcutaneous administration, intramuscular administration and intravenous administration), rectal administration and the like. For examples, suitable dosage forms for oral administration include tablets, capsules, granules, pulvis, pills, powders, lozenges, syrups and suspensions; suitable dosage forms for parenteral administration include aqueous or non-aqueous solutions or emulsions for injection; suitable dosage forms for rectal administration include suppositories using hydrophilic or hydrophobic carriers. The above-mentioned dosage forms may be made into dosage forms suitable for rapid release, delayed release or controlled release of the active ingredients as needed.

In another aspect, the present invention provides a method for inhibiting the activity of an IDH2 mutant, comprising administering to a subject in need thereof, the crystal of the compound of Formula I, the acid addition salt of the compound of Formula I or a hydrate or solvent thereof, the crystal of the mesylate of the compound of Formula I, or the pharmaceutical composition according to the present invention.

In still another aspect, the present invention provides a method for treating an IDH2 mutation-induced cancer, comprising administering to a subject in need thereof, the crystal of the compound of Formula I, the acid addition salt of the compound of Formula I or a hydrate or solvent thereof, the crystal of the mesylate of the compound of Formula I, or the pharmaceutical composition according to the present invention.

In yet another aspect, the present invention provides the crystal of the compound of Formula I, the acid addition salt of the compound of Formula I or a hydrate or solvent thereof, the crystal of the mesylate of the compound of Formula I, or the pharmaceutical composition according to the present invention for use in inhibiting the activity of an IDH2 mutant.

In a further aspect, the present invention provides the crystal of the compound of Formula I, the acid addition salt of the compound of Formula I or a hydrate or solvent thereof, the crystal of the mesylate of the compound of Formula I, or the pharmaceutical composition according to the present invention for use in the treatment of an IDH2 mutation-induced cancer.

In another aspect, the present invention provides use of the crystal of the compound of Formula I, the acid addition salt of the compound of Formula I or a hydrate or solvent thereof, the crystal of the mesylate of the compound of Formula I, or the above pharmaceutical composition in inhibiting the activity of an IDH2 mutant.

In still another aspect, the present invention provides use of the crystal of the compound of Formula I, the acid addition salt of the compound of Formula I or a hydrate or solvent thereof, the crystal of the mesylate of the compound of Formula I, or the above pharmaceutical composition in the treatment of an IDH2 mutation-induced cancer.

In yet another aspect, the present invention provides use of the crystal of the compound of Formula I, the acid addition salt of the compound of Formula I or a hydrate or solvent thereof, the crystal of the mesylate of the compound of Formula I, or the above pharmaceutical composition in the manufacture of a medicament for inhibiting the activity of an IDH2 mutant.

In a further aspect, the present invention provides use of the crystal of the compound of Formula I, the acid addition salt of the compound of Formula I or a hydrate or solvent thereof, the crystal of the mesylate of the compound of Formula I, or the above pharmaceutical composition in the manufacture of a medicament for the treatment of an IDH2 mutation-induced cancer.

The crystal of the compound of Formula I, the acid addition salt of the compound of Formula I or a hydrate or solvent thereof, the crystal of the mesylate of the compound of Formula I, or the above pharmaceutical composition according to the present invention may be used alone or in combination with other drugs for the treatment of an IDH2 mutation-induced cancer. The crystal of the compound of Formula I is the crystalline Form A or B of the compound of Formula I; optionally, the acid addition salt of the compound of Formula I is a mesylate of the compound of Formula I, a hydrochloride salt of the compound of Formula I, a sulfate of the compound of Formula I, a p-toluenesulfonate of the compound of Formula I, or a maleate of the compound of Formula I, or a hydrate or solvate of the above-mentioned addition salts, and the above-mentioned addition salts or the hydrates or solvates thereof are optionally in crystalline form or amorphous form; and the crystal of the mesylate of the compound of Formula I includes the crystalline Forms I, II, III, IV, V, VI, VII and VIII. In some embodiments, the IDH2 mutation-induced cancer is selected from the group consisting of glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, bile duct cancer, and angioimmunoblastic non-Hodgkin's lymphoma (NHL), and the like. In more specific embodiments, the cancer to be treated is selected from the group consisting of glioma, myelodysplastic syndrome (MDS), myeloproliferative neoplasm (MPN), acute myelogenous leukemia (AML), melanoma, chondrosarcoma, and vascular immunoblastic non-Hodgkin's lymphoma (NHL) and the like. In some embodiments, the cancer includes acute myelogenous leukemia (AML) or sarcoma.

In some embodiments of the present application, the IDH2 mutation is an IDH2/R140Q mutation or an IDH2/R172K mutation.

"IDH2 mutant" refers to IDH2 in which an IDH2/R140Q mutation form or an IDH2/R172K mutation form has occurred.

In the present invention, the X-ray powder diffraction spectrum of a sample is measured under the following conditions.

Instrument: BRUKER D2; pretreatment of a sample: direct compression; sample tray: single crystal silicon sample tray; initial shot slit: 0.6 nm; 2θ angle range: 5° to 40°; detector slit: 3 mm; Cu target, tube pressure and current: 30 KV, 10 mA.

In the present invention, the DSC spectrum is measured under the following conditions.

Instrument: METTLER TOLEDO DSC1; temperature range: 0° C. to 300° C.; heating rate: 10° C./min.

It should be noted that, in an X-ray powder diffraction (XRD) spectrum, a diffraction pattern of a crystalline compound is usually characteristic for a specific crystalline form. Relative intensities of the bands (especially at the low angles) may vary depending upon preferential orientation effects resulting from the differences of crystals' conditions, particle sizes, and other measuring conditions. Therefore, the relative intensities of diffraction peaks are not characteristic for a specific crystalline form. It is the relative positions of peaks rather than relative intensities thereof that should be paid more attention when judging whether a crystalline form is the same as a known crystalline form. In additional, as for any given crystalline form, there may be a slight error in the position of peaks, which is also well known in the field of crystallography. For example, the position of a peak may shift due to the change of a temperature, the movement of a sample or the calibration of an instrument and so on when analyzing the sample, and the measurement error of 2θ value is sometimes about ±0.2°. Accordingly, this error should be taken into consideration when identifying a crystal structure. Usually, the position of a peak is expressed in terms of 2θ angle or lattice spacing d in an XRD pattern and the simple conversion relationship therebetween is $d=\lambda/2 \sin\theta$, wherein d represents the lattice spacing, λ represents the wavelength of incident X-ray, and θ represents the diffraction angle. For the same crystalline form of the same compound, the position of peaks in an XRD spectrum thereof has similarity on the whole, and the error of relative intensities may be larger. In addition, it is necessary to point out that due to some factors such as reduced contents, parts of diffraction lines may be absent in the identification of a mixture. In this case, even a band may be characteristic for the given crystalline form without depending upon all the bands of a high purity sample.

DSC is used to measure a thermal transition temperature when absorbing or releasing heat due to the change of a crystal structure or the melting of a crystal. In a continuous analysis of the same crystalline form of the same compound, the error of a thermal transition temperature and a melting point is typically within a range of about ±5° C., generally within a range of about ±3° C. A compound with a given DSC peak or melting point means that the DSC peak or melting point may be varied within a range of ±5° C. DSC provides an auxiliary method to distinguish different crystalline forms. Different crystalline forms can be identified by their characteristically different transition temperatures. It is necessary to point out that the DSC peak or melting point of a mixture may vary over a wider range. Furthermore, because of the decomposition in the melting process of a substance, the melting temperature is related to a heating rate.

In the present invention, the term "therapeutically effective amount" refers to the amount of the medicament or agent which is not toxic but sufficient to achieve the desired effect. The effective amount may be determined individually and depends on the age and general condition of the receptor as well as the specific active substance. The effective amount in a specific case can be determined by a person skilled in the art through conventional experiments.

In the present invention, the term "pharmaceutically acceptable carrier" refers to those carriers which are administered together with an active ingredient, have no significant irritation to an organism and do not impair the bioactivity and property of the active compound. Other information regarding the carriers may be found in Remington: The Science and Practice of Pharmacy, 21st Ed., Lippincott, Williams & Wilkins (2005), the contents of which are incorporated herein by reference.

In the present invention, the term "solvate" means a physical association of a compound, including a crystalline form thereof, of the present invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include, for example, a hydrate, or acetonate.

In the present invention, the term "hydrate" is a solvate in which the solvent molecule is $H_2O$ that is present in a defined stoichiometric amount, and may, for example, include hemihydrate, monohydrate, dihydrate, or trihydrate.

In the present invention, the term "acid addition salt" refers to a salt formed by reacting an organic acid or an inorganic acid with a free base.

In the present invention, the term "molar ratio" and the term "ratio of the moles" are equivalent to each other.

In the present invention, the term "room temperature" refers to 20° C. to 25° C.

In the present invention, the term "concentrating under reduced pressure" means reducing the pressure by means of vacuum pumping to reduce the boiling point of a solvent, thereby evaporating the solvent and precipitating a solid.

In the present invention, the term "slurring" refers to a purification method in which a solid and a solvent are stirred together to contact sufficiently with each other so as to dissolve impurities by utilizing the difference in solubility of substances in the solvent.

In the present invention, the term "subject" includes humans and animals, for example, mammals (such as primates, cattle, horses, pigs, dogs, cats, mice, rats, rabbits, goats, sheep and birds, etc.).

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited.

The term "optionally" means that the subsequently described one or more events or circumstances may or may not occur, and that the description includes instances where said events or circumstances occur and instances in which it does not.

In the present invention, PK parameters are explained as follows: in the PK parameters, Tmax is the time to the maximum concentration ($T_{max}$); Cmax is the maximum plasma concentration; MRT(0-t) is the average residence time from time 0 to the final blood collection time point; $T_{1/2}$ is the half life; AUC(0-t) is the area under the plasma concentration-time curve from time 0 to the final blood collection time point; AUC(0-∞) is the area under the plasma concentration-time curve from time 0 to infinity.

SPECIFIC EMBODIMENTS

Figure 1:
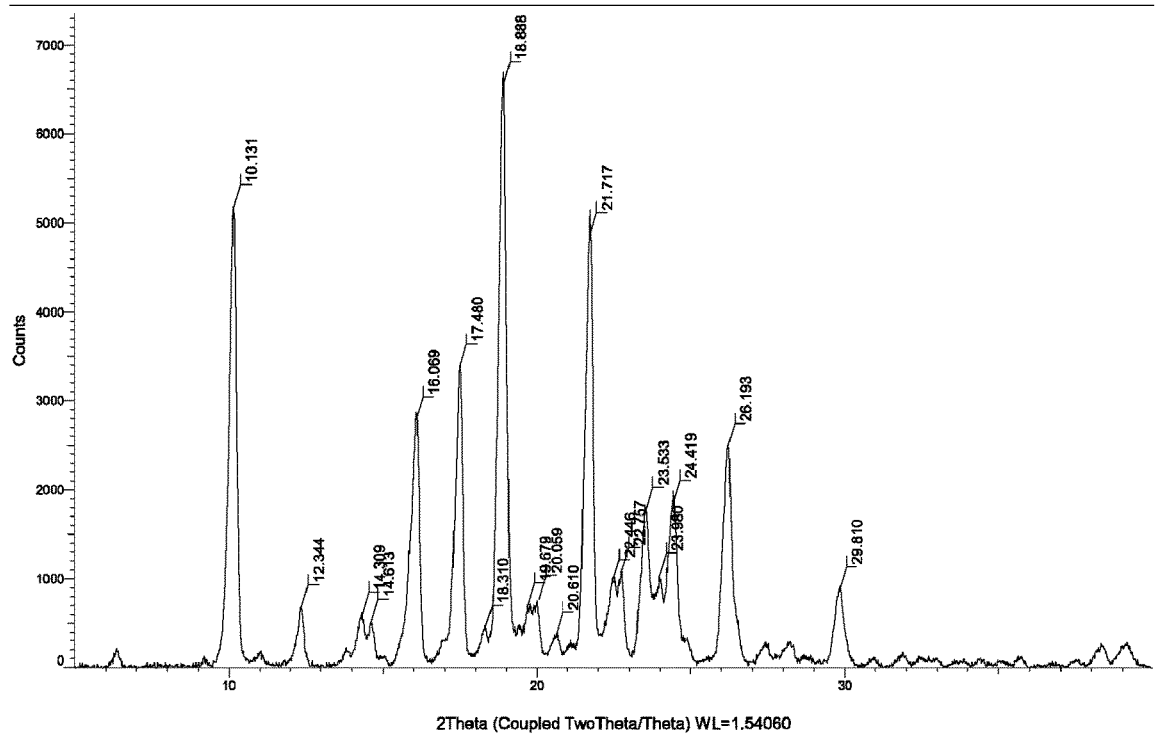
FIG. 1 is an X-ray powder diffraction pattern (XRPD) of the crystalline Form A of the compound of Formula I.
Figure 2:
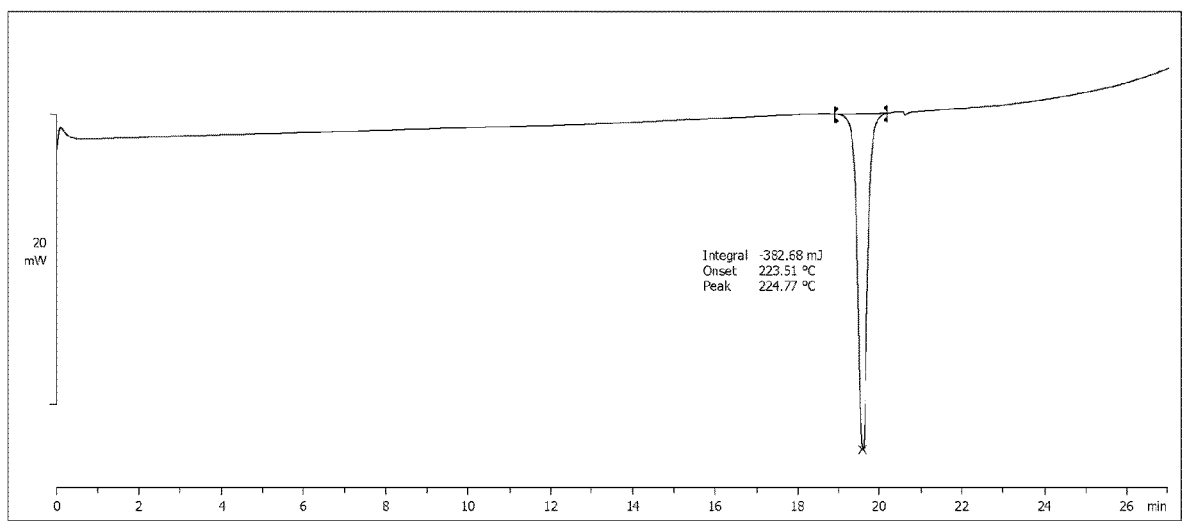
FIG. 2 is a differential scanning calorimetry (DSC) curve of the crystalline Form A of the compound of Formula I.
Figure 3:
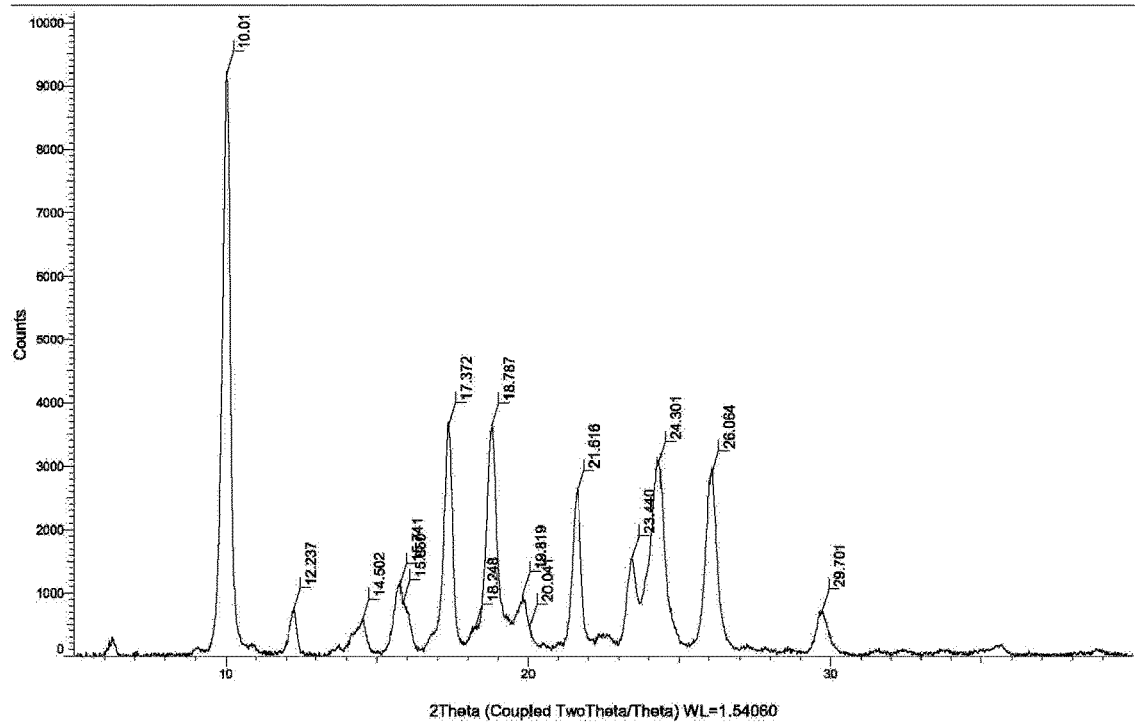
FIG. 3 is an X-ray powder diffraction pattern (XRPD) of the crystalline Form B of the compound of Formula I.
Figure 4:
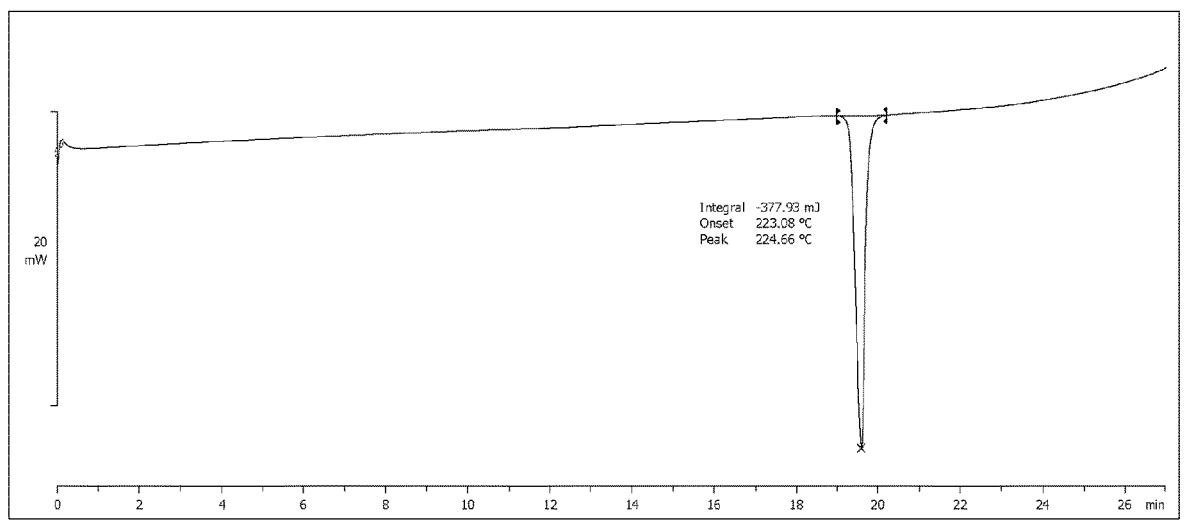
FIG. 4 is a differential scanning calorimetry (DSC) curve of the crystalline Form B of the compound of Formula I.

The following specific examples are provided to enable those skilled in the art to more clearly understand and practice the invention. They should not be construed as a limitation to the scope of the invention, but as mere illustrations and typical representatives of the invention. Those skilled in the art will understand that there are other synthetic routes involved for preparing the compounds of the present application, and ones provided below are non-limiting examples.

All operations involving raw materials that are susceptible to oxidation or hydrolysis are carried out under a nitrogen protection atmosphere. Unless indicated otherwise, raw materials used in the present invention are commercially available and directly used without further purification. Solvents used in the present invention are commercially available and directly used without any special treatments.

Column chromatography was performed using silica gel (200-300 mesh) produced by Qingdao Chemical Co., Ltd. Nuclear magnetic resonance chromatography (NMR) was measured using a Varian VNMRS-400 nuclear magnetic resonance meter; Liquid chromatography-mass spectrometry (LC/MS) was performed using FINNIGAN Thermo LCQ Advantage MAX, Agilent LC 1200 series (column: Waters Symmetry C18, ø4.6×50 mm, 5 micron, 35° C.) and using ESI (+) ion mode. The melting point tester is BUCHI B-545 melting point apparatus.

Example 1: Preparation of the Compound of Formula I

A: methyl 6-trifluoromethyl-pyridine-2-carboxylate

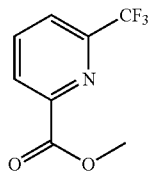

To a solution of 2-bromo-6-trifluoromethylpyridine (1.48 g, 6.55 mmol) in methanol (50.0 mL) were added in sequence palladium acetate (74.0 mg, 0.33 mmol), 1,1'-bis(diphenylphosphino)ferrocene (363.0 mg, 0.655 mmol) and triethylamine (0.92 g, 9.1 mmol) under the protection of nitrogen gas. The reaction solution reacted at 60° C. under a carbon monoxide atmosphere with 2 atmospheric pressures for 18 hours. After the reaction was completed, the reaction solution was cooled to room temperature and filtered. The filtrate was concentrated under vacuum and reduced pressure, and the resulting residue was purified by silica gel column chromatography to afford the title compound (0.9 g, yield: 67.0%).

2-Bromo-6-trifluoromethylpyridine was commercially available.

B: 6-(6-trifluoromethylpyridin-2-yl)-1,3,5-triazin-2,4(1H,3H)-dione

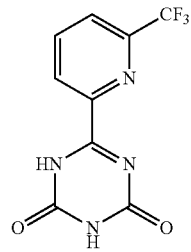 [SMILES: O=c1nc(-c2cccc(C(F)(F)F)n2)[nH]c(=O)[nH]1]

To a solution of sodium ethoxide (11.2 g, 165.0 mmol) in ethanol (200 mL) were added in sequence methyl 6-trifluoromethyl-pyridine-2-carboxylate (10.0 g, 48.7 mmol) and biuret (4.2 g, 40.7 mmol) under the protection of nitrogen gas. The mixture was heated to reflux for 2 hours and then cooled to room temperature. Then the reaction solution was concentrated under vacuum and reduced pressure, and the resulting residue was poured into water and adjusted to pH 7 with 6N hydrochloric acid solution. The resulting solid was filtered, and the filter cake was washed with water and then dried to afford the title compound (5.0 g, yield: 47.5%).

C: 2,4-dichloro-6-(6-trifluoromethylpyridin-2-yl)-1,3,5-triazine

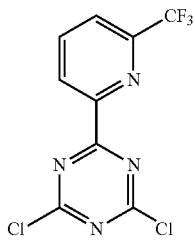 [SMILES: FC(F)(F)c1cccc(-c2nc(Cl)nc(Cl)n2)n1]

A mixture solution of 6-(6-trifluoromethylpyridin-2-yl)-1,3,5-triazin-2,4(1H,3H)-dione (15.0 g, 58.1 mmol) and phosphorus oxychloride (200 mL) reacted at 100° C. for 2 hours under the protection of nitrogen gas and then cooled to room temperature. The reaction solution was concentrated under vacuum and reduced pressure, and the resulting residue was poured into a saturated aqueous solution of sodium bicarbonate. The resulting mixture was extracted with ethyl acetate (2×100 mL), and the organic phase was dried over anhydrous sodium sulfate and then filtered. The filtrate was concentrated under vacuum to afford the title compound (10.0 g, yield: 58.3%).

D: 4-chloro-6-(6-trifluoromethylpyridin-2-yl)-N-(2-(trifluoromethyl)pyridin-4-yl)-1,3,5-triazin-2-amine

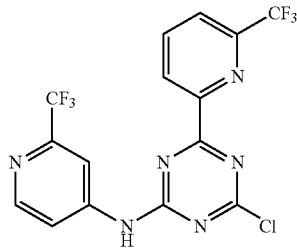 [SMILES: FC(F)(F)c1cc(Nc2nc(Cl)nc(-c3cccc(C(F)(F)F)n3)n2)ccn1]

To a solution of 2,4-dichloro-6-(6-trifluoromethylpyridin-2-yl)-1,3,5-triazine (5.0 g, 16.9 mmol) in tetrahydrofuran (100 mL) were added 4-amino-2-trifluoromethylpyridine (3.3 g, 20.3 mmol) and sodium bicarbonate (2.14 g, 25.3 mmol). The mixture reacted at 70° C. for 8 hours and then cooled to room temperature. The reaction solution was then concentrated under vacuum and reduced pressure, and the resulting residue was purified by silica gel column chromatography to afford the title compound (6.5 g, yield: 91.2%).

4-Amino-2-trifluoromethylpyridine was commercially available.

E: 4-(tert-butoxyamino)-6-(6-(trifluoromethyl)pyridin-2-yl)-N-(2-(trifluoromethyl)pyridin-4-yl)-1,3,5-triazin-2-amine (the Compound of Formula I)

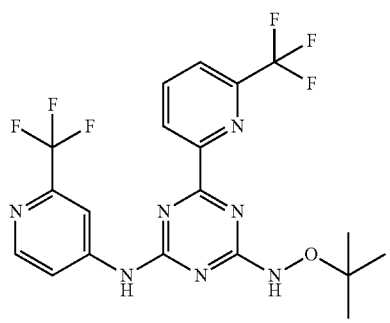 [SMILES: CC(C)(C)ONc1nc(Nc2ccnc(C(F)(F)F)c2)nc(-c2cccc(C(F)(F)F)n2)n1]

To a solution of 4-chloro-6-(6-trifluoromethylpyridin-2-yl)-N-(2-(trifluoromethyl)pyridin-4-yl)-1,3,5-triazin-2-amine (39.7 g, 94.5 mmol) in tetrahydrofuran (400 mL) were added O-tert-butylhydroxylamine hydrochloride (17.7 g, 140.9 mmol) and sodium bicarbonate (31.7 g, 377 mmol). The mixture reacted at 70° C. for 8 hours and then cooled to room temperature. Then the reaction solution was filtered, the filtrate was concentrated under vacuum and reduced pressure, and the resulting residue was purified by silica gel column chromatography to afford the title compound (30.0 g, yield: 67%).

Mp: 226.1~228° C.

MS m/z[ESI]: 474.14 [M+H]$^+$.

$^1$H-NMR (400 MHz, DMSO-d6): δ=11.00 (s, 1H), 10.84 (s, 1H), 8.74 (s, 1H), 8.57 (t, J=6.5 Hz, 2H), 8.31 (t, J=7.9 Hz, 1H), 8.11 (d, J=7.7 Hz, 1H), 7.99 (s, 1H), 1.28 (s, 9H).

Example 2: Preparation of the Crystalline Form A of the Compound of Formula I

At room temperature, to tetrahydrofuran (60 mL) was added the compound of Formula I (5.0 g, 10.6 mmol) obtained in Example 1, stirred and dissolved to obtain a clear solution. Then the solution was concentrated under reduced pressure, and the resulting solid was dried under vacuum at 80° C. for 4 hours, Mp: 224.6° C.~226° C.

Example 3: Preparation of the Crystalline Form A of the Compound of Formula I

At room temperature, to 1,4-dioxane (100 mL) was added the compound of Formula I (5.0 g, 10.6 mmol) obtained in Example 1, stirred and dissolved to obtain a clear solution. Then the solution was concentrated under reduced pressure, and the resulting solid was dried under vacuum at 80° C. for 4 hours, Mp: 224.6° C.~226° C.

Example 4: Preparation of the Crystalline Form A of the Compound of Formula I

To the compound of Formula I (5.0 g, 10.6 mmol) obtained in Example 1 was added dichloromethane (50 mL), and slurred under reflux for 2 hours, and then the reaction temperature was lowered to room temperature. The resulting mixture was filtered, and the filter cake was dried under vacuum at 80° C. for 4 hours, Mp: 224.6° C.~226° C.

Example 5: Preparation of the Crystalline Form A of the Compound of Formula I

To the compound of Formula I (5.0 g, 10.6 mmol) obtained in Example 1 was added n-heptane (50 mL), and slurred at room temperature for 2 hours. The resulting mixture was filtered, and the filter cake was dried under vacuum at 80° C. for 4 hours, Mp: 224.6° C.~226° C.

Example 6: Preparation of the Crystalline Form B of the Compound of Formula I

At room temperature, to the compound of Formula I (5.0 g, 10.6 mmol) obtained in Example 1 was added ethyl acetate (50 mL), stirred and dissolved to obtain a clear solution. Then the solution was concentrated under reduced pressure, and the resulting solid was dried under vacuum at 80° C. for 4 hours, Mp: 226.1° C.~228° C.

Example 7: Preparation of the Hydrochloride Salt of the Compound of Formula I

To a solution of the compound of Formula I (1.0 g, 2.1 mmol) obtained in Example 1 in ethyl acetate (10 mL) was added dropwise a prepared solution of 14.6% by mass hydrogen chloride (3.2 mmol) in ethanol (0.8 g) at room temperature. After stirring for 2 hours, a solid was precipitated from the reaction solution, and then filtered. The filter cake was dried under vacuum at 80° C., Mp: 177.2~179° C.

Example 8: Preparation of the Sulfate of the Compound of Formula I

To a solution of the compound of Formula I (1.0 g, 2.1 mmol) obtained in Example 1 in ethyl acetate (10 mL) was added dropwise a prepared solution (1.9 mL) of 1.67 mol/L dilute sulfuric acid in ethanol at room temperature. After stirring for 2 hours, a solid was precipitated from the reaction solution, and then filtered. The filter cake was dried under vacuum at 80° C., Mp: 181.2~183° C.

Example 9: Preparation of the p-Toluenesulfonate of the Compound of Formula I P-toluenesulfonic acid monohydrate (0.6 g, 3.1 mmol) was dissolved in acetone (2 mL) at room temperature. Then, to a solution of the compound of Formula I (1.0 g, 2.1 mmol) obtained in Example 1 in acetone (10 mL) was added dropwise the pre-formulated solution of p-toluenesulfonic acid in acetone. After stirring for 2 hours, a solid was precipitated from the reaction solution, and then filtered. The filter cake was dried under vacuum at 80° C., Mp: 173.9~176° C.

Example 10: Preparation of the Maleate of the Compound of Formula I

To a solution of the compound of Formula I (2.45 g, 5.2 mmol) obtained in Example 1 in acetone (10 mL) was added maleic acid (0.58 g, 5.0 mmol) at room temperature. After stirring for 2 hours, a solid was precipitated from the reaction solution, and then filtered. The filter cake was dried under vacuum at 80° C., Mp: 171.3~173° C.

Example 11: Preparation of the Crystalline Form I of the Mesylate of the Compound of Formula I To a solution of the compound of Formula I (3.0 g, 6.3 mmol) obtained in Example 1 in methyl tert-butyl ether (90 mL) was added dropwise methanesulfonic acid (0.61 g, 6.3 mmol) at room temperature. After stirring for 1 hour, a solid was precipitated from the reaction solution, and then filtered. The filter cake was dried under vacuum at 80° C., Mp: 148.2~150.2° C.

Example 12: Preparation of the Crystalline Form II of the Mesylate of the Compound of Formula I To a solution of the compound of Formula I (3.0 g, 6.3 mmol) obtained in Example 1 in methyl tert-butyl ether (90 mL) was added dropwise methanesulfonic acid (0.61 g, 6.3 mmol) at a reflux temperature. After stirring for 1 hour, the reaction temperature was lowered to room temperature, and a solid was precipitated from the reaction solution and then filtered. The filter cake was dried under vacuum at 80° C., Mp: 187.1~189.1° C.

Example 13: Preparation of the Crystalline Form III of the Mesylate of the Compound of Formula I To a solution of the compound of Formula I (5.0 g, 10.6 mmol) obtained in Example 1 in ethyl acetate (100 mL) was added dropwise methanesulfonic acid (1.21 g, 12.6 mmol) at room temperature. After stirring for 2 hours, a solid was precipitated from the reaction solution, and then filtered. The filter cake was dried under vacuum at 80° C., Mp: 150.9~152.9° C.

Example 14: Preparation of the Crystalline Form IV of the Mesylate of the Compound of Formula I To a solution of the compound of Formula I (5.0 g, 10.6 mmol) obtained in Example 1 in ethyl acetate (100 mL) was added dropwise methanesulfonic acid (3.05 g, 31.5 mmol) at room temperature. After stirring for 2 hours, a solid was precipitated from the reaction solution, and then filtered. The filter cake was dried under vacuum at 80° C. for 4 hours and then further dried under vacuum at 100° C. for 4 hours, Mp: 155.0~157.0° C.

Example 16: Preparation of the Crystalline Form V of the Mesylate of the Compound of Formula I To a solution of the compound of Formula I (5.0 g, 10.6 mmol) obtained in Example 1 in acetone (100 mL) was added dropwise methanesulfonic acid (3.05 g, 31.5 mmol) at room temperature. After stirring for 2 hours, a solid was precipitated from the reaction solution, and then filtered. The filter cake was dried under vacuum at 80° C., Mp: 151.8~153.8° C.

Example 17: Preparation of the Crystalline Form VI of the Mesylate of the Compound of Formula I To a solution of the compound of Formula I (5.0 g, 10.6 mmol) obtained in Example 1 in acetonitrile (100 mL) was added dropwise methanesulfonic acid (1.21 g, 12.6 mmol) at room temperature. After stirring for 2 hours, a solid was precipitated from the reaction solution, and then filtered. The filter cake was dried under vacuum at 80° C., Mp: 145.5~147.5° C.

Example 18: Preparation of the Crystalline Form VII of the Mesylate of the Compound of Formula I To a solution of the compound of Formula I (5.0 g, 10.6 mmol) obtained in Example 1 in acetonitrile (100 mL) was added dropwise methanesulfonic acid (3.05 g, 31.5 mmol) at room temperature. After stirring for 2 hours, a solid was precipitated from the reaction solution, and then filtered. The filter cake was dried under vacuum at 80° C., Mp: 140.1~142.1° C.

Example 19: Preparation of the Crystalline Form VIII of the Mesylate of the Compound of Formula I The compound of Formula 1 (3.0 g, 6.3 mmol) was dissolved in methyl tert-butyl ether (90 mL), and the reaction solution was heated to reflux. Then, a solution of methylenesulfonic acid (0.61 g, 6.3 mmol) in methyl tert-butyl ether (60 mL) was slowly added dropwise thereto. The reaction solution was refluxed to react for 1 hour, and then cooled to room temperature followed by filteration. The filter cake was dried under vacuum at 90° C. to afford a white solid, MP: 188.8-191.2° C.

Example 20: Preparation of the Crystalline Form VIII of the Mesylate of the Compound of Formula I The compound of Formula 1 (3.0 g, 6.3 mmol) was dissolved in methyl tert-butyl ether (90 mL), and the reaction solution was heated to reflux. Then, a solution of methylenesulfonic acid (0.31 g, 3.1 mmol) in methyl tert-butyl ether (30 mL) was slowly added dropwise thereto. The reaction solution was refluxed to react for 1 hour, and then cooled to room temperature followed by filteration. The filter cake was dried under vacuum at 90° C. to afford a white solid, MP: 188.8-191.2° C.

Example 21: Hygroscopicity Test of Various Salts of the Compound of Formula I The various acid addition salts of the compound of Formula I were tested according to "Guiding Principles for Drug Hygroscopicity Test" described in the Chinese Pharmacopoeia, 2010 edition, Part II, Appendix XIX J. The increased weights by hygroscopy of the samples were calculated respectively, and the results are shown in Table 11.

TABLE 11

Hygroscopicity Test Results

| Sample Names | Increased Weights by Hygroscopy, HR = 80% ± 2(%) |
|---|---|
| The mesylate (Example 12) | 1.0 |
| The hydrochloride salt (Example 7) | 0.9 |
| The sulfate (Example 8) | 1.3 |
| The p-toluenesulfonate (Example 9) | 0.7 |
| Maleate (Example 10) | 2.2 |
| The crystalline Form VIII of the mesylate (Example 19) | 1.0 |

Example 22: Stability Test of Various Salts of the Compound of Formula I

The stability of the various acid addition salts of the compound of Formula I were tested according to the method described in the Chinese Pharmacopoeia, 2010 edition, Part II, Appendix XIX C. The results are shown in Table 12.

TABLE 12

Stability Test Results

| Sample Names | Purity before test | Purity after high temperature and high humidity test |
|---|---|---|
| The mesylate (Example 12) | 98.82% | 99.22% |
| The hydrochloride salt (Example 7) | 98.85% | 99.62% |
| The sulfate (Example 8) | 99.30% | 93.58% |
| The p-toluenesulfonate (Example 9) | 98.79% | 97.63% |
| The crystalline Form VIII of the mesylate (Example 19) | 98.82% | 99.22% |

Example 23: Inhibitory Activity Test Against IDH2

The inhibitory activity of the compound of the present application against IDH2 (R172K, 40-end) was determined by using the following method. The inhibitory activity was expressed as $IC_{50}$ values, i.e., the concentration of the compound required to achieve 50% inhibition of IDH2 activity.

Materials and Methods:

The inhibitory activity of a compound against IDH2 (R172K, 40-end) was determined by the decrease of a helper factor NADPH (reduced coenzyme II). The test compound was pre-incubated with an enzyme and NADPH, and then a reaction was initiated by the addition of a-KG, and performed for 120 minutes under a linear condition. Then, the reaction was terminated by the addition of diaphorase (lipoamide dehydrogenase) and the corresponding substrate resazurin. Diaphorase terminated the IDH2m reaction by decreasing the available helper factor NADPH, which oxidized NADPH to NADP (oxidized coenzyme II), and reduced resazurin to highly fluorescent resorufin. The amount of remaining helper factor NADPH after a specific reaction time was quantified via an easily detectable fluorophore.

Specifically, 2.5 µl of a 3-fold gradient diluted test compound was added to a 384-well plate, and then 5 µl of a reaction buffer (20 mM Tris-HCl, PH7.5; 150 mM NaCl; 10 mM $MgCl_2$; 10 mM $MnCl_2$; 0.4 mg/ml BSA and 2 mM DTT) containing 80 nM IDH2 (R172K, 40-end) and 40 µM NADPH was added. Then, the resulting test mixture was incubated for 120 minutes at a temperature of 23° C., and then 2.5 µl of the reaction buffer containing 4 mM a-KG was added to initiate the reaction. After incubating for 120 minutes at room temperature, 5 µl of a termination mixture (0.4 U/ml diaphorase and 40 µM resazurin) prepared with the reaction buffer was added to convert resazurin to resorufin to determine the remaining NADPH. After incubating for 10 minutes at a temperature of 23° C., a fluorescence value was determined through Flexstation 3 at Ex535/Em595. The results are shown in Table 13: the compound of Formula I has a better inhibitory activity than AG-221.

TABLE 13

Inhibitory activity against IDH2

| Sample Names | $IC_{50}$ (nM) |
|---|---|
| The compound of Formula I | 32 |
| AG-221 | 68 |

Example 24: Pharmacokinetic Test

Healthy male adult rats (7-9 weeks old) were used, each group of animals (3 male rats) was intragastrically administered once at a single dose of 5 mg/kg. The animals in the intragastric administration group were fasted overnight before this study. The fasting time period was from 10 hours before administration to 4 hours after administration.

Blood samples were taken at 0.25, 0.5, 1, 2, 4, 6, 8 and 24 h after administration. The animals were anesthetized with isoflurane using a small animal anesthesia machine, and then 0.3 mL whole blood samples were taken from the fundus venous plexus. The blood samples were placed in heparin anticoagulant tubes, and centrifuged for 5 min at 4° C. and 4000 rpm. The resulting plasma samples were transferred to centrifuge tubes, and stored at −80° C. until analysis.

Verified liquid chromatography-tandem mass spectrometry (LC-MS/MS) method was used to analyze the plasma samples. Plasma concentration-time data of individual animals were analyzed using WinNonlin (Professional Edition, version 6.3; Pharsight Company) software. The non-compartmental model was introduced for concentration analysis. The pharmacokinetic parameters (PK parameters) of the compounds were calculated. The results are shown in Table 14. The compound of Formula I has a good in vivo metabolic level and a long half-life, and its plasma concentration is higher than AG-221 at the same dosage.

TABLE 14

PK parameters of the compound of Formula I and AG-221

| PK parameters | The compound of Formula I | AG-221 |
|---|---|---|
| Dosage (mg/kg) | 5 | 5 |
| $T_{1/2}$ (h) | 12.0 | 3.73 |
| $T_{max}$ (h) | 5.0 | 4.00 |
| $C_{max}$ (ng/mL) | 589 | 479 |
| AUC(0-∞) (ng*h/mL) | 10838 | 5385 |

Example 25: Pharmacokinetic Test

1. Test Material

Species: SD rats;

Level: SPF;

Number and gender: 20, males;

Body weight: 200~220 g;

Source: Shanghai Xipuer Bikai Experimental Animal Co., Ltd. SCXK (Shanghai) 2013-0016.

2. Test Method

Twenty male SPF SD rats were randomly divided into 4 groups, fasted (free access to water) overnight, and then intragastrically administered with 50 mg/kg of the crystalline Form I of the mesylate of the compound of Formula I (Example 11), 50 mg/kg of the crystalline Form II of the mesylate of the compound of Formula I (Example 12), 50 mg/kg of the crystalline Form VIII of the mesylate of the compound of Formula I (Example 19) and 50 mg/kg of the hydrochloride salt of the compound of Formula I (Example 7), respectively (in basic group). Blood samples (0.2~0.3 mL) were taken from the orbital of the rats at the blood collection time points 0.25 h, 0.5 h, 1 h, 2 h, 3 h, 4 h, 6 h, 8 h, 10 h, 24 h, 30 h and 48 h after administration. The whole blood collected was then placed in EDTA-K2 centrifuge tubes, stored at 4° C., and centrifuged for 10 min at a speed of 4000 rpm at 4° C. within 0.5 h to separate plasma. After the collection of all the plasma, it was stored at −20° C. within 1 h. Pharmacokinetic parameters (PK parameters) were calculated using DAS 3.2.1 software according to the non-compartment statistical moment theory, and the results are shown in Table 15.

TABLE 15

PK parameters after the intragastric administration of 50 mg/kg (in free base) of the compounds in SD rats

| PK parameters | The crystalline Form I of the mesylate of the compound of Formula I | The crystalline Form II of the mesylate of the compound of Formula I | The crystalline Form VIII of the mesylate of the compound of Formula I | The hydrochloride salt of the compound of Formula I |
|---|---|---|---|---|
| Tmax (h) | 6.60 | 8.80 | 8.80 | 10.6 |
| Cmax (ng/mL) | 1728 | 2102 | 2102 | 1642 |
| MRT(0-t) (h) | 16.5 | 15.0 | 15.0 | 18.02 |
| $T_{1/2}$(h) | 10.4 | 9.53 | 9.53 | 13.67 |
| AUC(0-t) (ng*h/mL) | 43925 | 42249 | 42249 | 48570.9 |
| AUC(0-∞) (ng*h/mL) | 47369 | 43976 | 43976 | 55252.1 |

What is claimed is:

1. Crystalline Form I of a methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I:

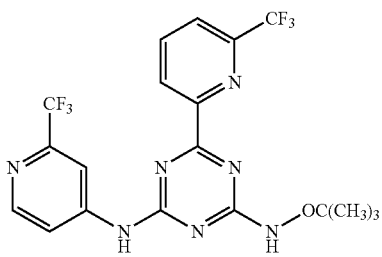

Formula I wherein the crystalline form is characterized by an X-ray powder diffraction pattern having X-ray powder diffraction peaks (2θ) expressed by values at 6.2°, 12.1°, 20.2°, and 25.0°±0.2° (2θ).

2. The crystalline Form I according to claim 1, wherein the crystalline Form I is further characterized by an X-ray powder diffraction pattern having additional X-ray powder diffraction peaks (2θ) expressed by values at 18.3°, 22.7°, and 24.6°±0.2° (2θ).

3. The crystalline Form I according to claim 1, wherein the crystalline Form I is further characterized by an X-ray powder diffraction pattern having additional X-ray powder diffraction peaks (2θ) expressed by values at 17.8°, 18.3°, 21.2°, 22.7°, 23.6°, 24.6°, and 27.0°±0.2° (2θ).

4. The crystalline Form I according to claim 1, wherein the crystalline Form I is further characterized by an X-ray powder diffraction pattern having additional X-ray powder diffraction peaks (2θ) expressed by values at 13.0°, 13.9°, 17.8°, 18.3°, 21.2°, 22.7°, 23.6°, 24.6°, 25.0°, and 27.0°±0.2° (2θ).

Figure 5:
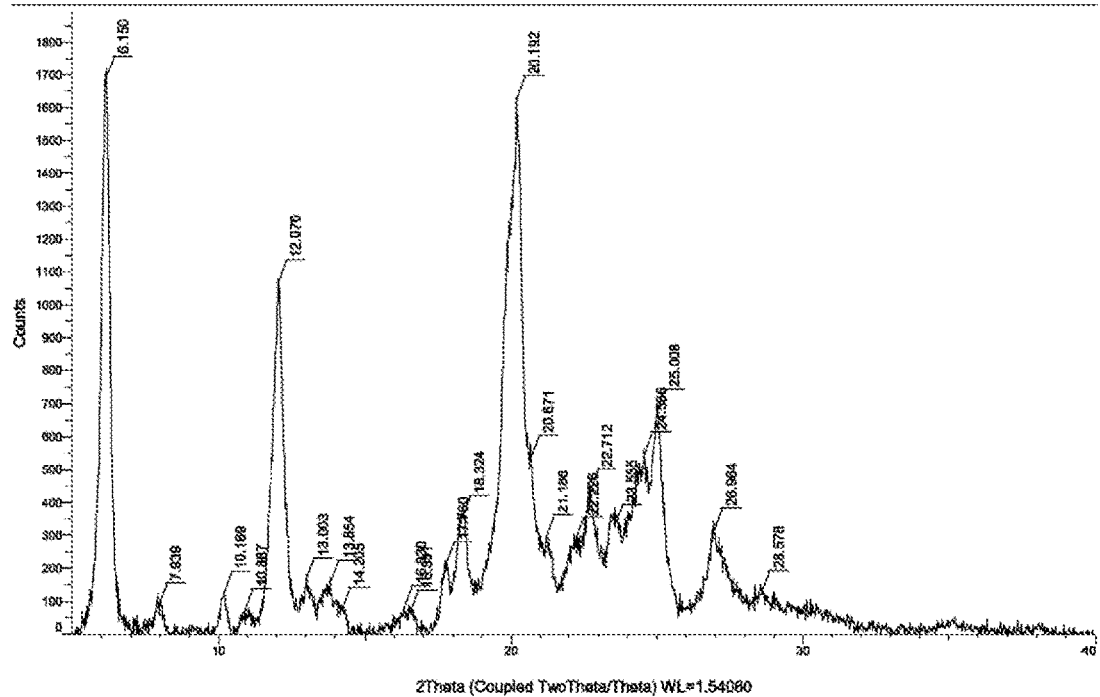
FIG. 5 is an X-ray powder diffraction pattern (XRPD) of the crystalline Form I of the mesylate of the compound of Formula I.
Figure 6:
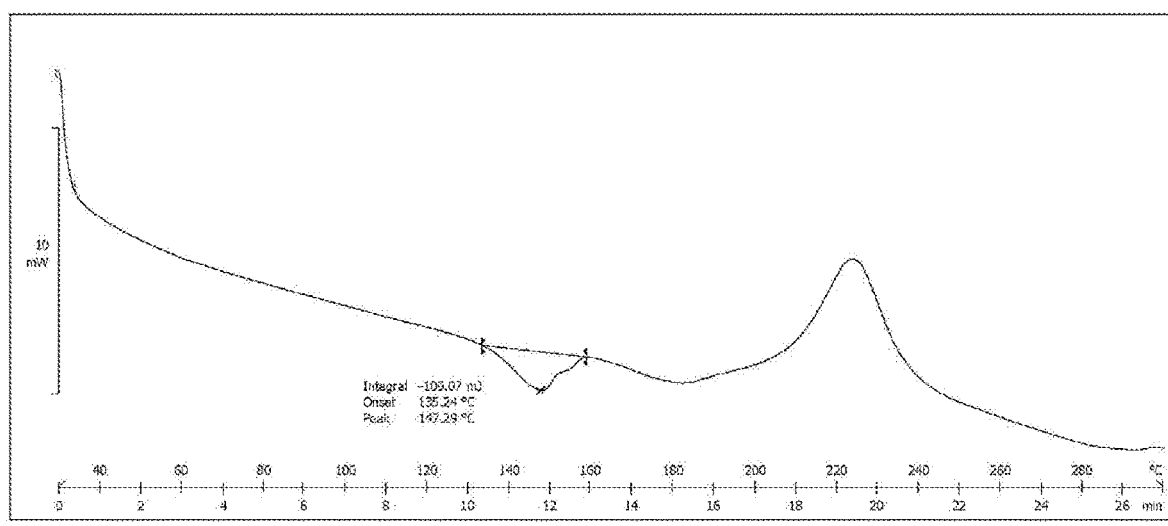
FIG. 6 is a differential scanning calorimetry (DSC) curve of the crystalline Form I of the mesylate of the compound of Formula I.
Figure 7:
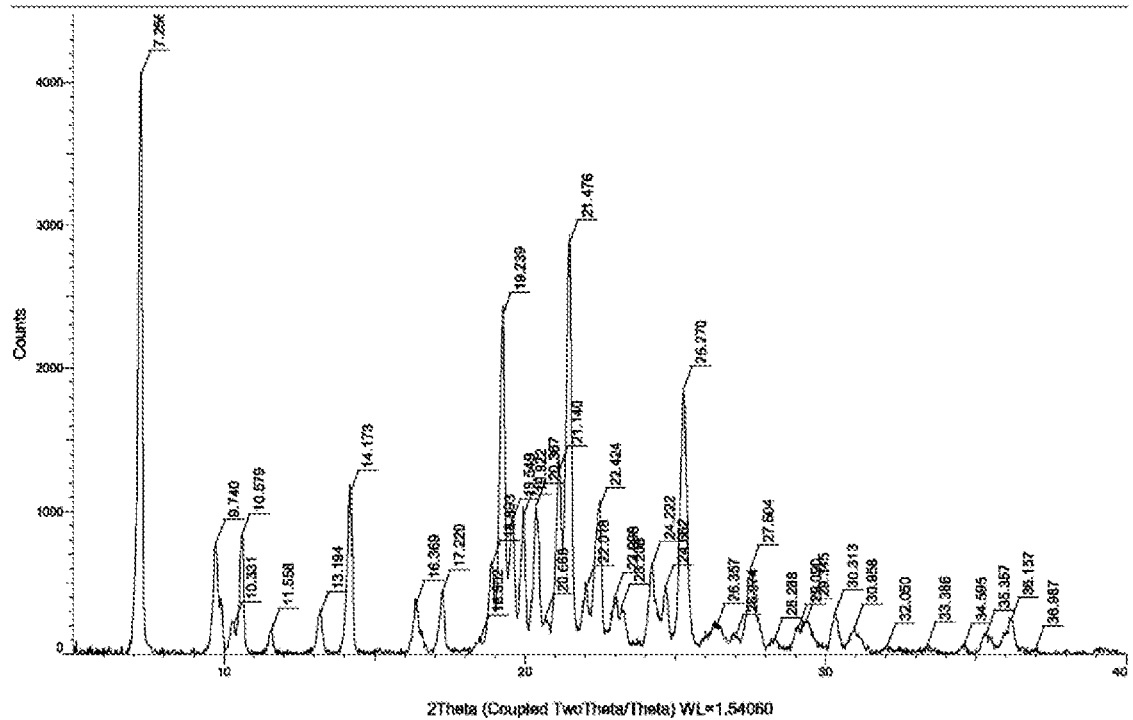
FIG. 7 is an X-ray powder diffraction pattern (XRPD) of the crystalline Form II of the mesylate of the compound of Formula I.
Figure 8:
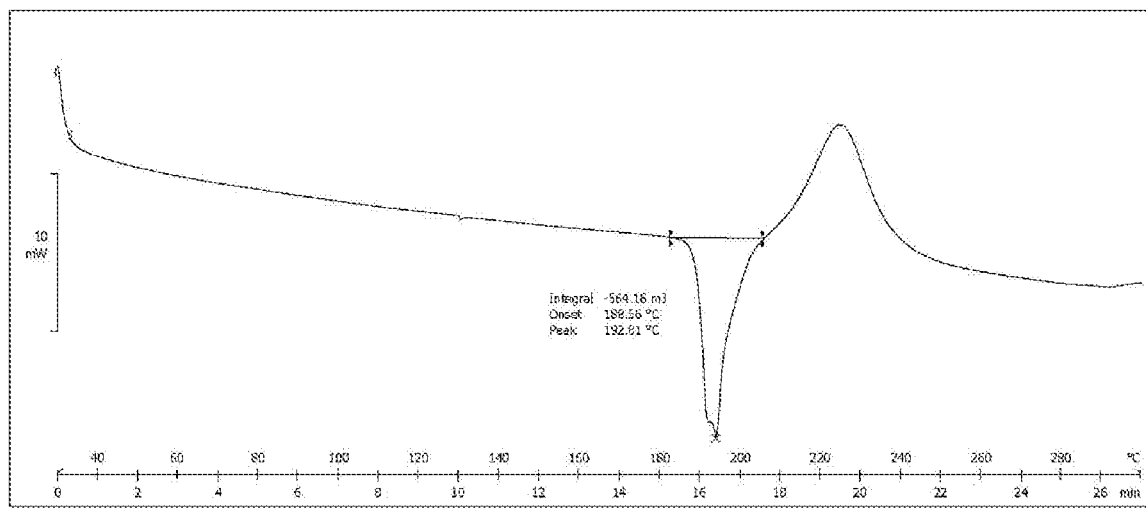
FIG. 8 is a differential scanning calorimetry (DSC) curve of the crystalline Form II of the mesylate of the compound of Formula I.
Figure 9:
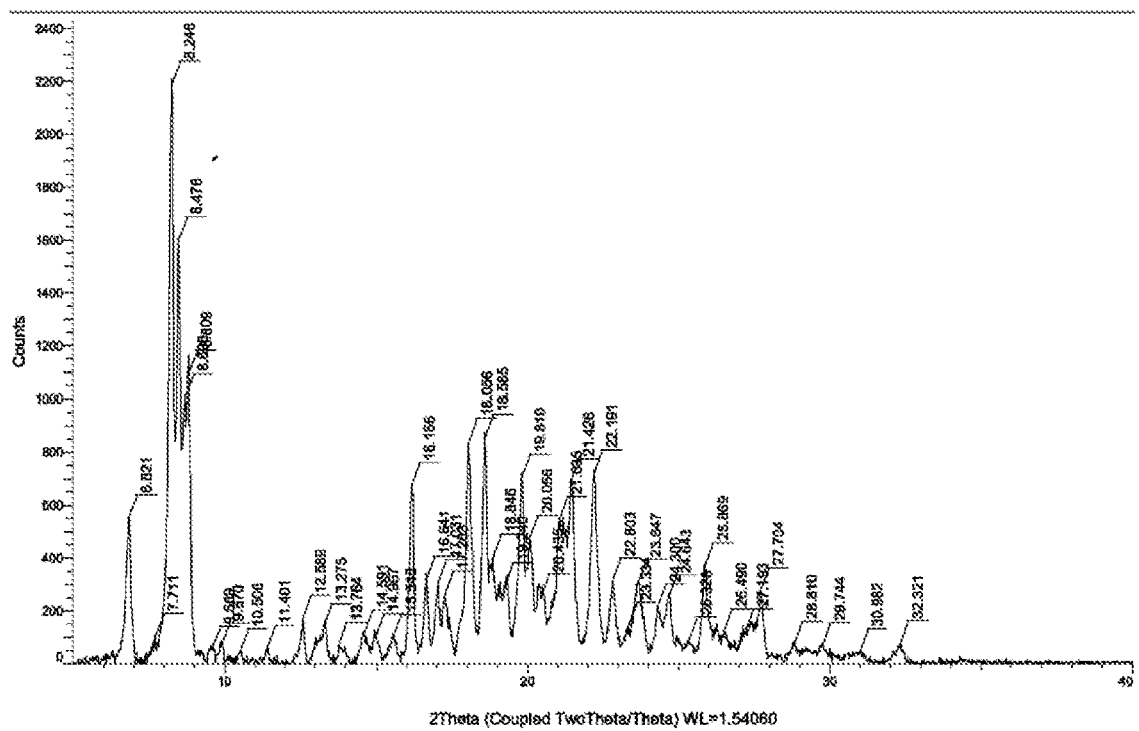
FIG. 9 is an X-ray powder diffraction pattern (XRPD) of the crystalline Form III of the mesylate of the compound of Formula I.
Figure 10:
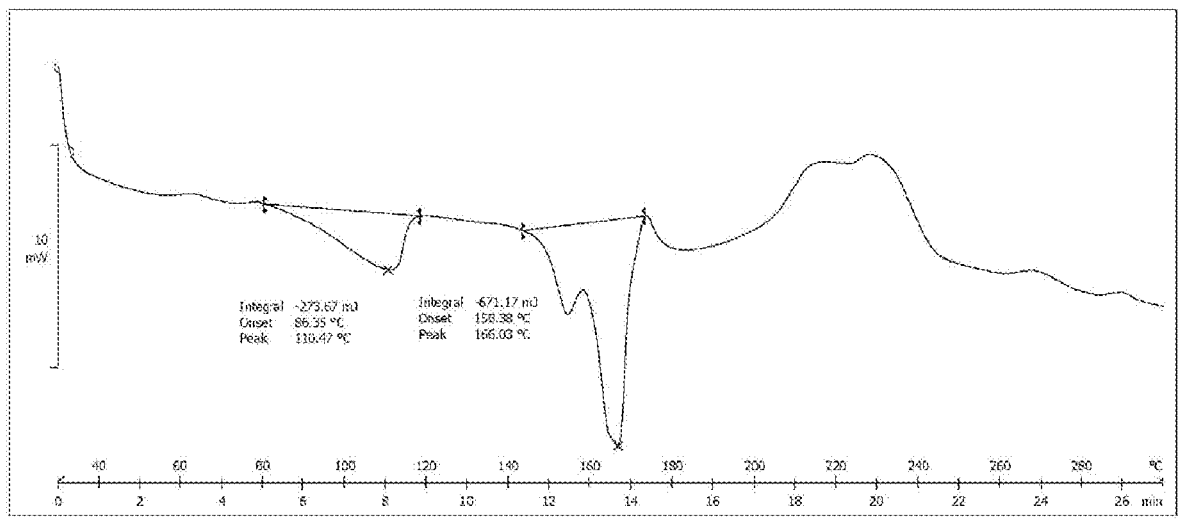
FIG. 10 is a differential scanning calorimetry (DSC) curve of the crystalline Form III of the mesylate of the compound of Formula I.
Figure 11:
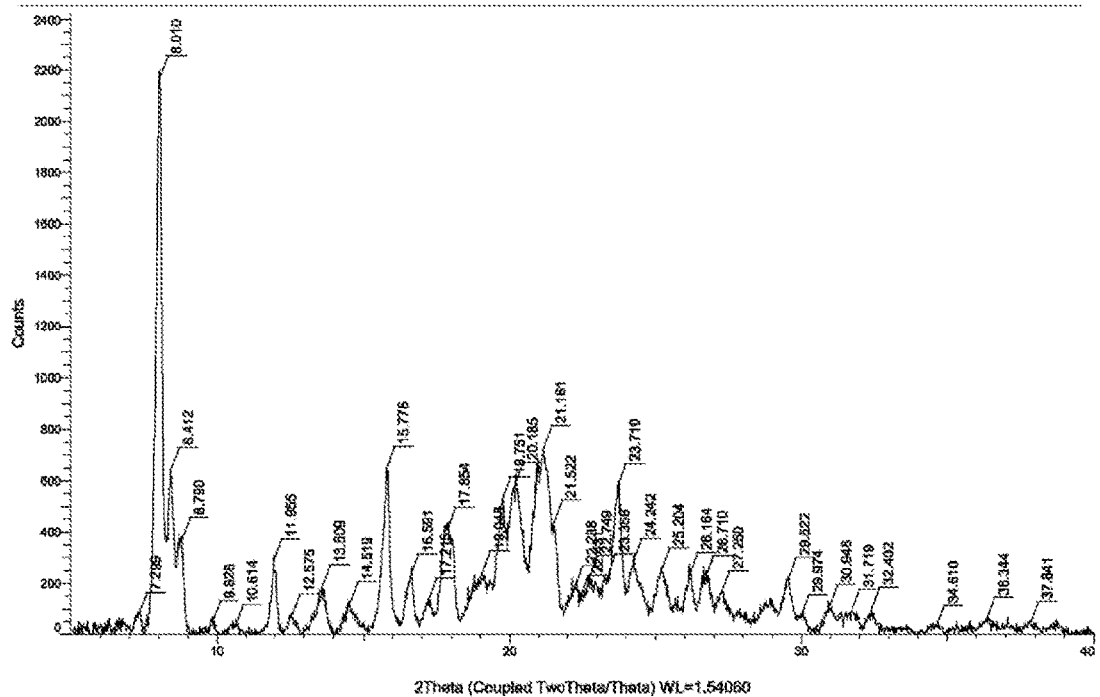
FIG. 11 is an X-ray powder diffraction pattern (XRPD) of the crystalline Form IV of the mesylate of the compound of Formula I.
Figure 12:
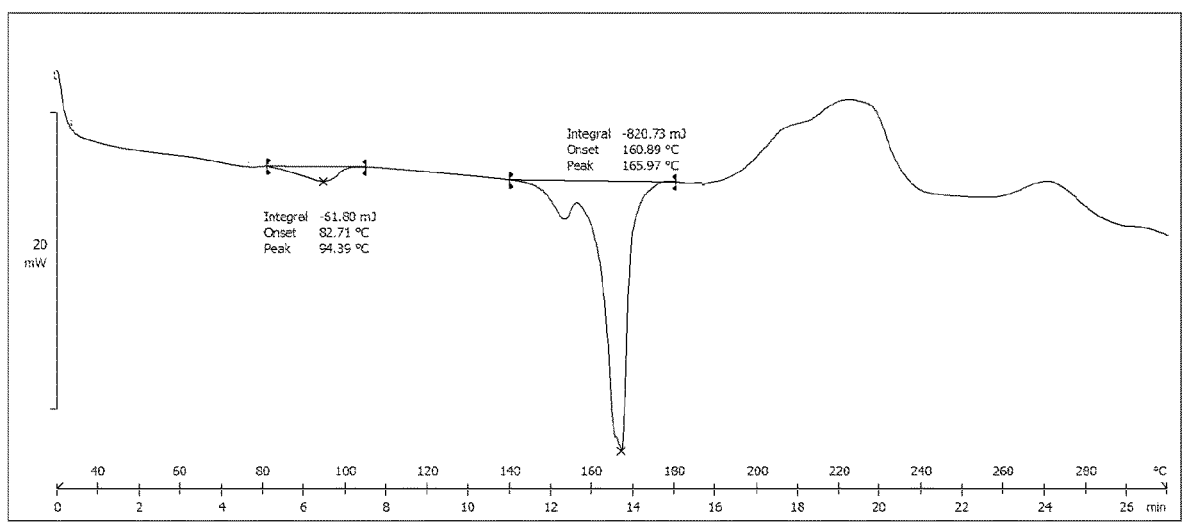
FIG. 12 is a differential scanning calorimetry (DSC) curve of the crystalline Form IV of the mesylate of the compound of Formula I.
Figure 13:
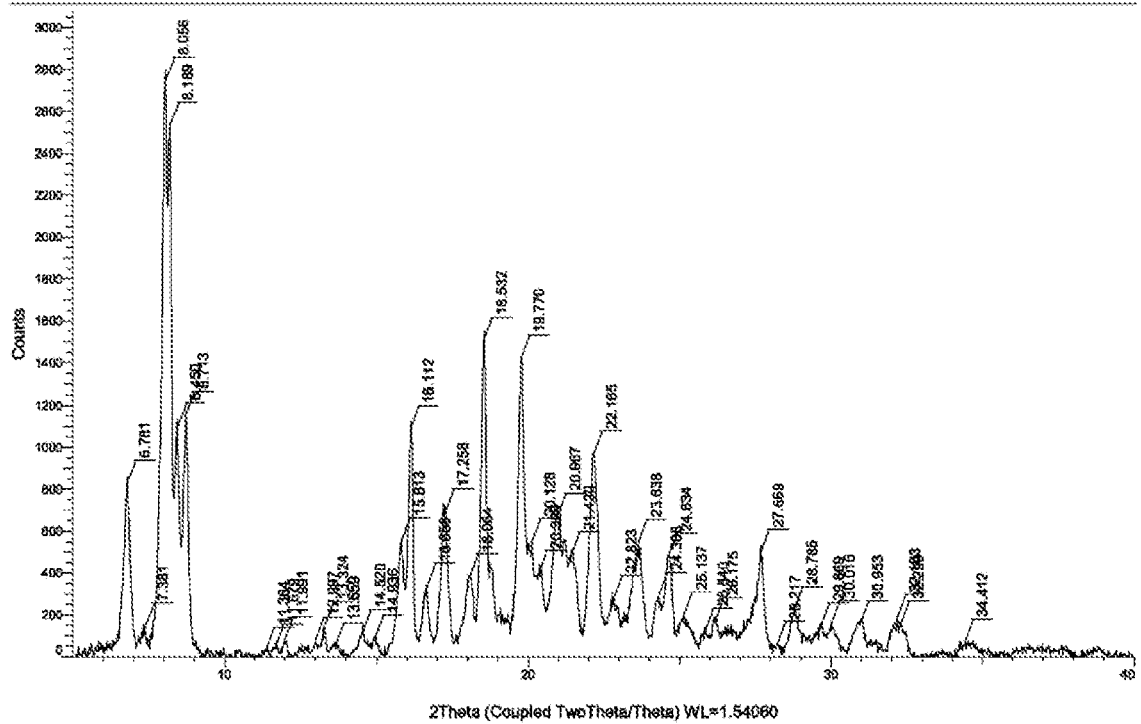
FIG. 13 is an X-ray powder diffraction pattern (XRPD) of the crystalline Form V of the mesylate of the compound of Formula I.
Figure 14:
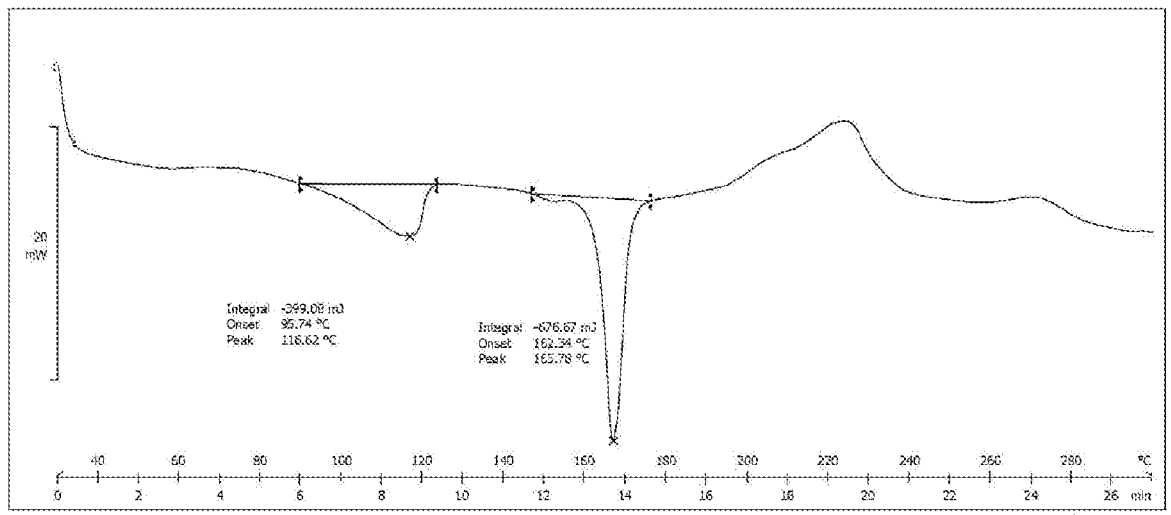
FIG. 14 is a differential scanning calorimetry (DSC) curve of the crystalline Form V of the mesylate of the compound of Formula I.
Figure 15:
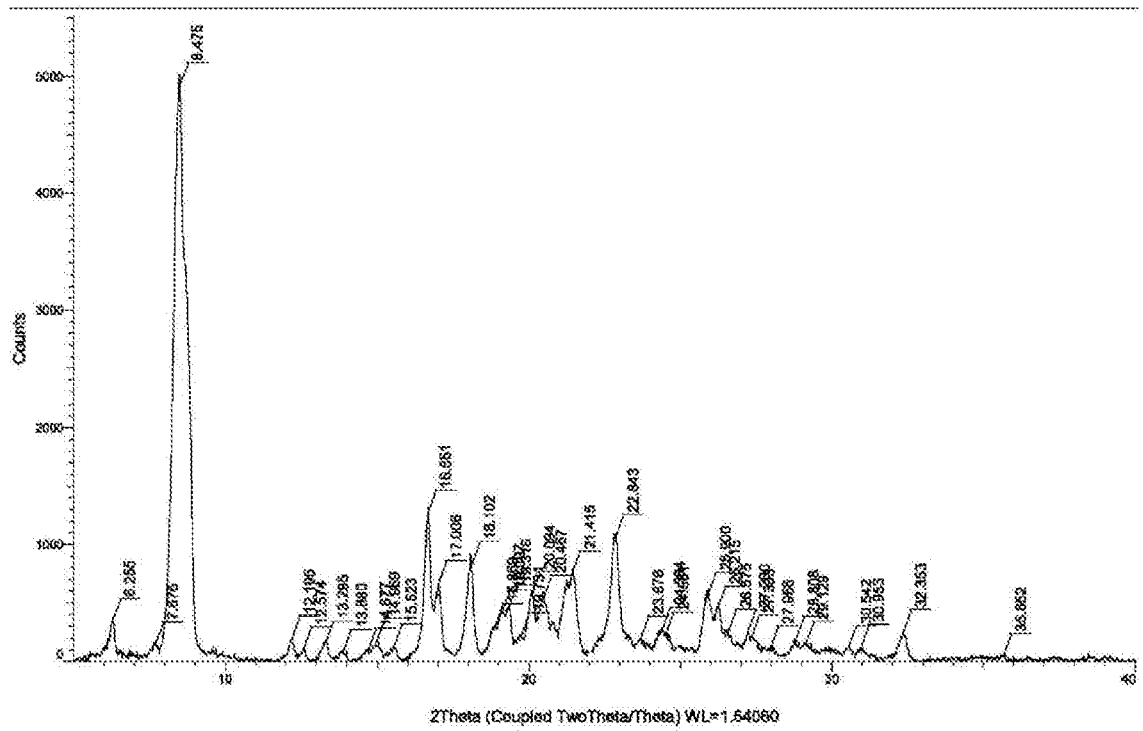
FIG. 15 is an X-ray powder diffraction pattern (XRPD) of the crystalline Form VI of the mesylate of the compound of Formula I.
Figure 16:
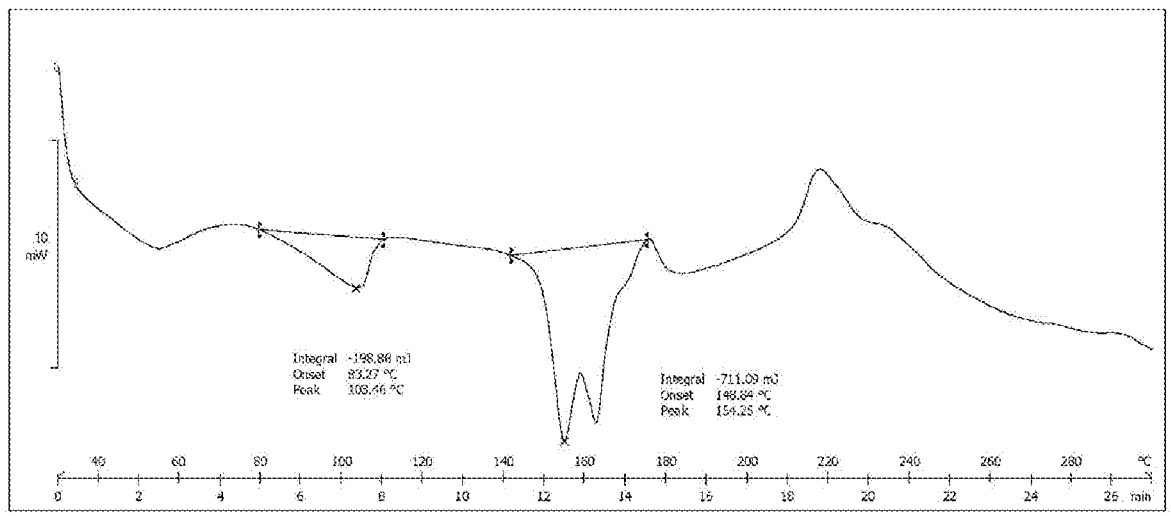
FIG. 16 is a differential scanning calorimetry (DSC) curve of the crystalline Form VI of the mesylate of the compound of Formula I.
Figure 17:
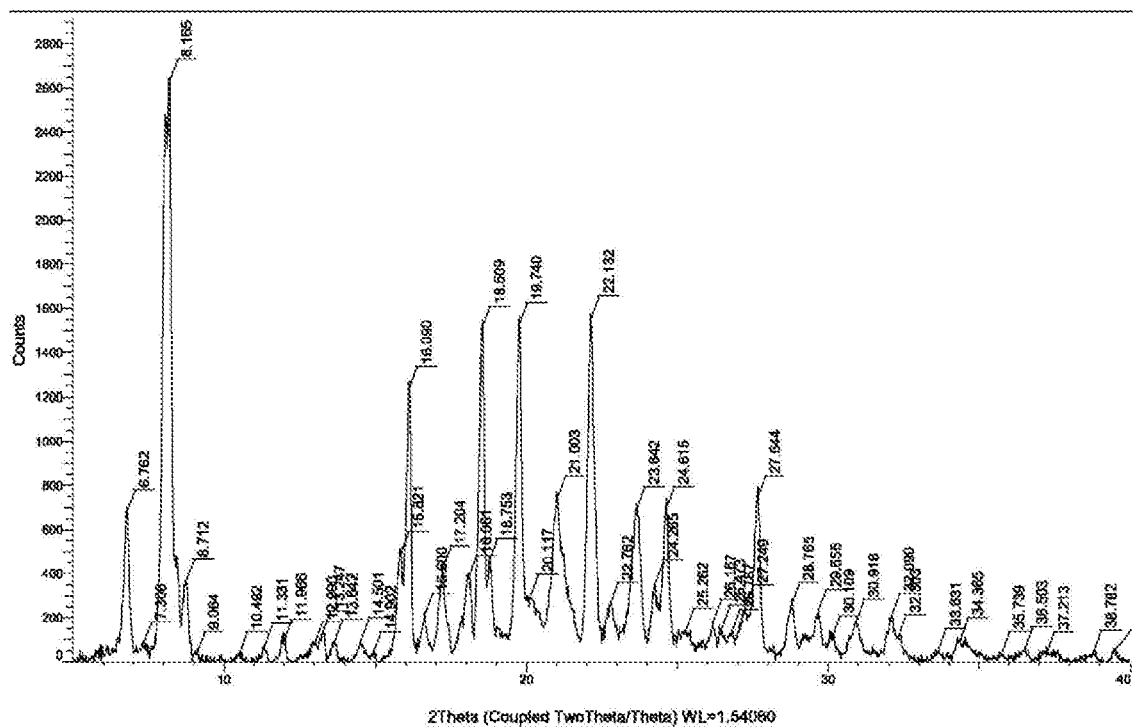
FIG. 17 is an X-ray powder diffraction pattern (XRPD) of the crystalline Form VII of the mesylate of the compound of Formula I.
Figure 18:
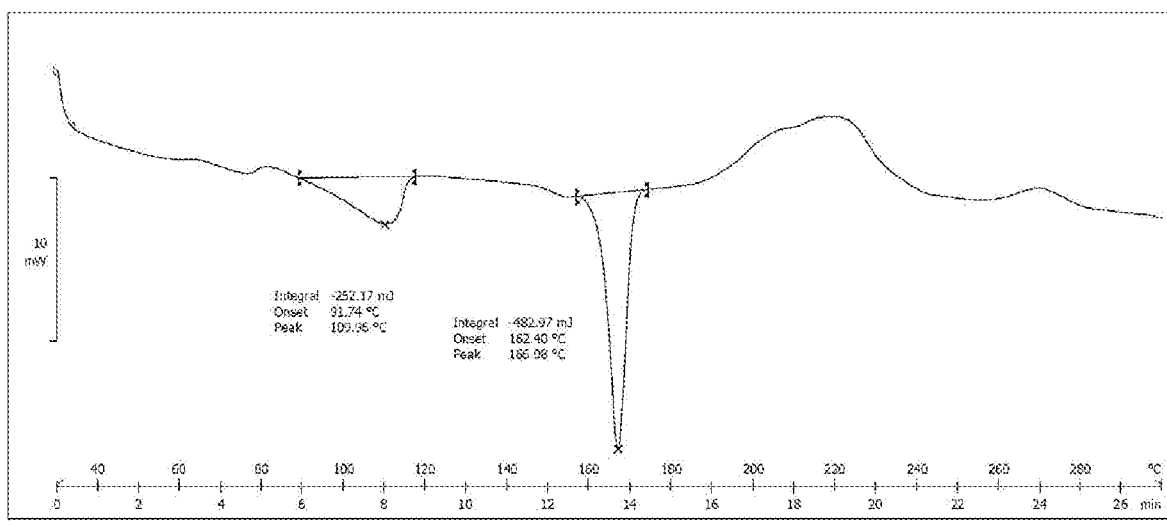
FIG. 18 is a differential scanning calorimetry (DSC) curve of the crystalline Form VII of the mesylate of the compound of Formula I.
Figure 19:
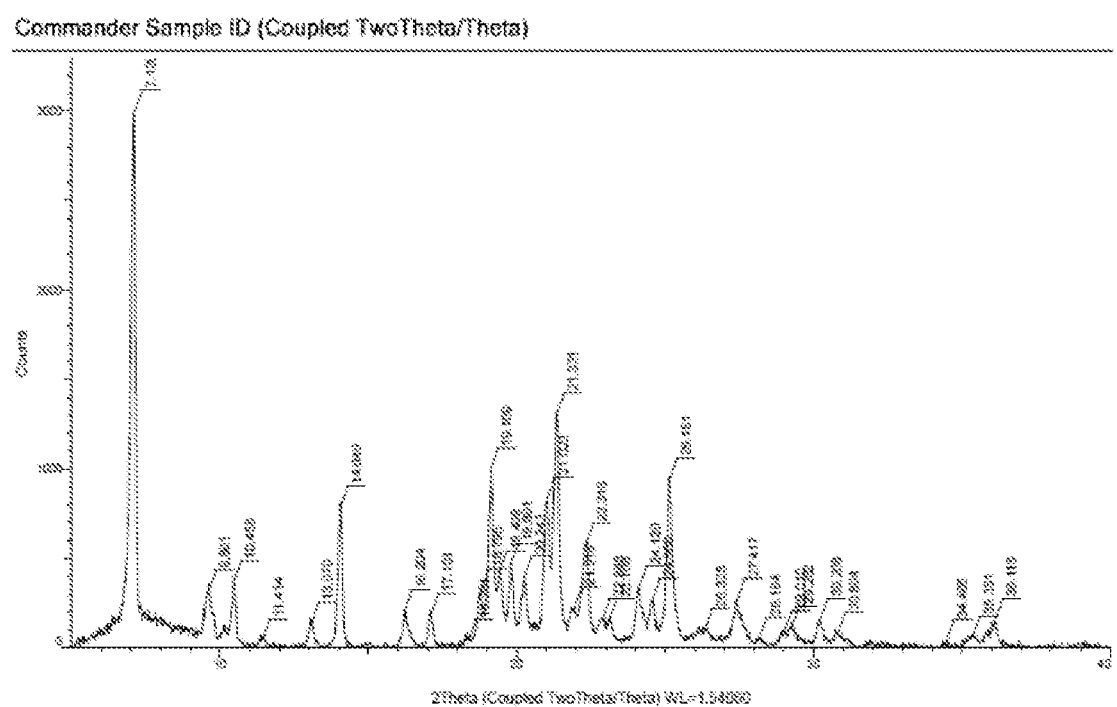
FIG. 19 is an X-ray powder diffraction pattern (XRPD) of the crystalline Form VIII of the mesylate of the compound of Formula I.

5. The crystalline Form I according to claim 1, wherein the crystalline form is characterized by an X-ray powder diffraction pattern as shown in FIG. 5.

6. A pharmaceutical composition comprising a pharmaceutically acceptable carrier and the crystalline Form I of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I according to claim 1.

7. A method for treating an isocitrate dehydrogenase 2 mutation-induced cancer in a subject, comprising administering to a subject in need thereof the crystalline Form I of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I according to claim 1.

8. The method according to claim 7, wherein the isocitrate dehydrogenase 2 mutation-induced cancer is selected from the group consisting of glioblastoma, myelodysplastic syndrome, myeloproliferative neoplasm, acute myelogenous leukemia, sarcoma, melanoma, non-small cell lung cancer, chondrosarcoma, bile duct cancer, and angioimmunoblastic non-Hodgkin's lymphoma.

9. A method for treating an isocitrate dehydrogenase 2 mutation-induced cancer in a subject, comprising administering to a subject in need thereof the pharmaceutical composition according to claim 6.

10. The method according to claim 9, wherein the isocitrate dehydrogenase 2 mutation-induced cancer is selected from the group consisting of glioblastoma, myelodysplastic syndrome, myeloproliferative neoplasm, acute myelogenous leukemia, sarcoma, melanoma, non-small cell lung cancer, chondrosarcoma, bile duct cancer, and angioimmunoblastic non-Hodgkin's lymphoma.

11. A process for preparing the crystalline Form I of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I according to claim 1:

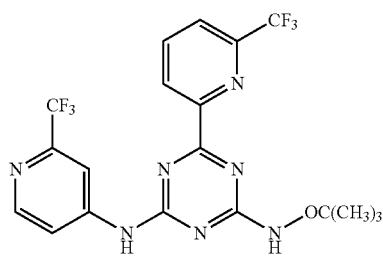

Formula I wherein the process comprises the following steps:

(i) dissolving 4-(tert-butoxyamino)-6-(6-(trifluoromethyl)pyridin-2-yl)-N-(2-(trifluoromethyl)pyridin-4-yl)-1,3,5-triazin-2-amine of Formula I below in methyl tert-butyl ether:

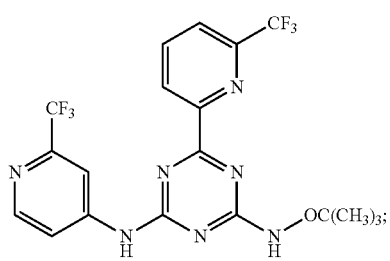

Formula I (ii) adding methanesulfonic acid dropwise to the solution formed in step (i) above at room temperature;

(iii) precipitating the crystalline Form I of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I above from the solution formed in step (ii) above;

(iv) isolating the crystalline Form I of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I above via filtration; and (v) drying the crystalline Form I of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I above.

12. Crystalline Form II of a methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I:

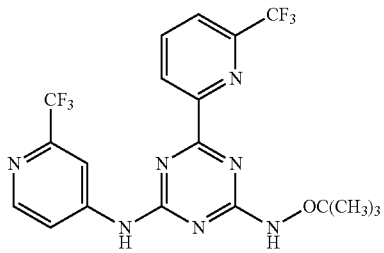

Formula I wherein the crystalline form is characterized by an X-ray powder diffraction pattern having X-ray powder diffraction peaks (2θ) expressed by values at 7.3°, 14.2°, 19.2°, 21.1°, 21.5°, and 25.3°±0.2° (2θ).

13. The crystalline Form II according to claim 12, wherein the crystalline Form II is further characterized by an X-ray powder diffraction pattern having additional X-ray powder diffraction peaks (2θ) expressed by values at 9.7°, 10.6°, 19.5°, 19.9°, 20.4°, and 22.4°±0.2° (2θ).

14. The crystalline Form II according to claim 12, wherein the crystalline Form II is further characterized by an X-ray powder diffraction pattern having additional X-ray powder diffraction peaks (2θ) expressed by values at 9.7°, 10.6°, 11.6°, 16.4°, 18.9°, 19.5°, 19.9°, 20.4°, 22.0°, 22.4°, 24.2°, 24.7°, and 27.5°±0.2° (2θ).

15. The crystalline Form II according to claim 12, wherein the crystalline Form II is further characterized by an X-ray powder diffraction pattern having additional X-ray powder diffraction peaks (2θ) expressed by values at 9.7°, 10.6°, 11.6°, 13.2°, 16.4°, 17.2°, 18.9°, 19.5°, 19.9°, 20.4°, 22.0°, 22.4°, 23.0°, 23.2°, 24.2°, 24.7°, and 27.5°±0.2° (2θ).

16. A pharmaceutical composition comprising a pharmaceutically acceptable carrier and the crystalline Form II of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I according to claim 12.

17. A method for treating an isocitrate dehydrogenase 2 mutation-induced cancer in a subject, comprising administering to a subject in need thereof the crystalline Form II of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I according to claim 12.

18. The method according to claim 17, wherein the isocitrate dehydrogenase 2 mutation-induced cancer is selected from the group consisting of glioblastoma, myelodysplastic syndrome, myeloproliferative neoplasm, acute myelogenous leukemia, sarcoma, melanoma, non-small cell lung cancer, chondrosarcoma, bile duct cancer, and angioimmunoblastic non-Hodgkin's lymphoma.

19. A process for preparing the crystalline Form II of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I according to claim 12:

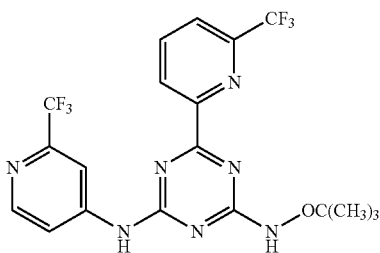

Formula I wherein the process comprises the following steps:

(i) dissolving 4-(tert-butoxyamino)-6-(6-(trifluoromethyl)pyridin-2-yl)-N-(2-(trifluoromethyl)pyridin-4-yl)-1,3,5-triazin-2-amine of Formula I below in methyl tert-butyl ether:

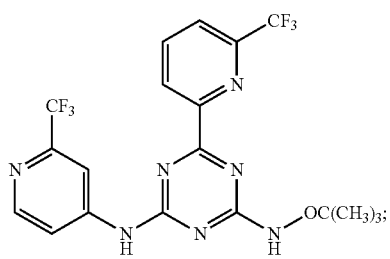

Formula I (ii) adding methanesulfonic acid dropwise to the solution formed in step (i) above at a reflux temperature;

(iii) cooling the solution formed in step (ii) above to room temperature;

(iv) precipitating the crystalline Form II of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I above from the solution formed in step (iii) above;

(v) isolating the crystalline Form II of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I above via filtration; and (vi) drying the crystalline Form II of the methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I above.

20. Crystalline Form VIII of a methanesulfonic acid salt of 4-(tert-butoxyamino)-6-(6-(trifluoromethyl)pyridin-2-yl)-N-(2-(trifluoromethyl)pyridin-4-yl)-1,3,5-triazin-2-amine of Formula I:

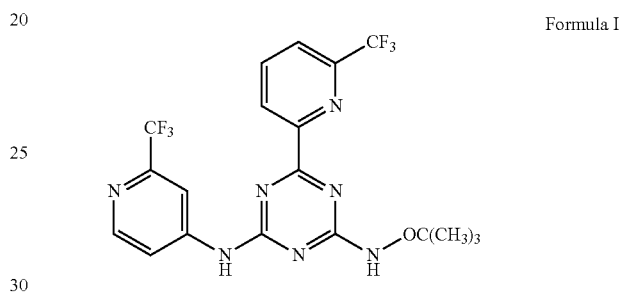

Formula I wherein the crystalline form is characterized by an X-ray powder diffraction pattern having X-ray powder diffraction peaks (2θ) expressed by values at 7.12°, 14.05°, 19.11°, 21.02°, 21.33°, and 25.15°±0.2° (2θ).

* * * * *